(12) United States Patent
Takechi et al.

(10) Patent No.: US 9,664,642 B2
(45) Date of Patent: May 30, 2017

(54) TFT ION SENSOR AND TFT ION SENSOR APPARATUS USING THE SAME

(71) Applicant: NLT Technologies, Ltd., Kanagawa (JP)

(72) Inventors: Kazushige Takechi, Kanagawa (JP); Hiroshi Haga, Kanagawa (JP); Shinnosuke Iwamatsu, Yamagata (JP); Seiya Kobayashi, Yamagata (JP); Yutaka Abe, Yamagata (JP); Toru Yahagi, Yamagata (JP)

(73) Assignee: NLT TECHNOLOGIES, LTD., Kanagawa (JP)

( * ) Notice: Subject to any disclaimer, the term of this patent is extended or adjusted under 35 U.S.C. 154(b) by 62 days.

(21) Appl. No.: 14/671,582

(22) Filed: Mar. 27, 2015

(65) Prior Publication Data

US 2015/0276663 A1    Oct. 1, 2015

(30) Foreign Application Priority Data

Mar. 28, 2014    (JP) .................................. 2014-068159

(51) Int. Cl.
*G01N 27/414* (2006.01)
*H01L 29/786* (2006.01)

(52) U.S. Cl.
CPC ....... *G01N 27/414* (2013.01); *G01N 27/4145* (2013.01); *H01L 29/7869* (2013.01); *G01N 27/4148* (2013.01)

(58) Field of Classification Search
CPC .............. G01N 27/414; G01N 27/4145; H01L 29/7869
See application file for complete search history.

(56) References Cited

U.S. PATENT DOCUMENTS 5,431,883 A * 7/1995 Barraud ............... G01N 27/414
257/253
8,968,499 B2    3/2015 Hiroya et al.
(Continued)

FOREIGN PATENT DOCUMENTS

JP    2010-192599    9/2010
JP    2012-013933    1/2012
(Continued)

OTHER PUBLICATIONS

Yan et al., "Polycrystalline Silicon Ion Sensitive Field", Effect Transistors "Applied Physics Letters", vol. 86, 053901 (2005).
(Continued)

*Primary Examiner* — Jose R Diaz
(74) *Attorney, Agent, or Firm* — Young & Thompson

(57) ABSTRACT

The ion sensors using TFT or MOSFET are low in the measurement sensitivity so that it is difficult to detect an extremely small amount of sensing-target substance. A TFT ion sensor includes both a gate electrode (a silicon substrate) and a reference electrode, in which the electrostatic capacitance of a gate insulating film (a thermal oxide film) is set to be larger than the electrostatic capacitance of an ion sensitive insulating film. Therefore, it is possible to detect the concentration of ions, hormones, and the like in a sensing-target substance from the shift in the threshold voltage of the gate-source voltage to source-drain current property.

20 Claims, 12 Drawing Sheets

(56) References Cited

U.S. PATENT DOCUMENTS

2008/0063566 A1* 3/2008 Matsumoto ........ G01N 33/5438
422/68.1
2012/0003434 A1 1/2012 Hiroya et al.

FOREIGN PATENT DOCUMENTS

JP 2012-073101 4/2012
JP 2013-076656 4/2013

OTHER PUBLICATIONS

Chou et al., "Temperature Effect of a-Si:H pH-ISFET", "Sensors and Actuators", B62, 92-96 (2000).
Koike et al., "Ion-Sensitive Characteristics of an Electrolyte-Solution-Gate ZnO/ZnMgO Heterojunction Field-Effect Transistor as a Biosensing Transducer".
"Japanse Journal of Applied Physics", vol. 46, L865-L867 (2007).

* cited by examiner

Vout=Vs

Vgs=Vg−Vs

Vout=Vg−Vgs $$\begin{cases} Vg-1.5 \text{ (ELECTRIC DOUBLE LAYER POTENTIAL DIFFERENCE : } -0.1V) \\ Vg-1.0 \text{ (ELECTRIC DOUBLE LAYER POTENTIAL DIFFERENCE : } 0V) \\ Vg-0.5 \text{ (ELECTRIC DOUBLE LAYER POTENTIAL DIFFERENCE : } +0.1V) \end{cases}$$

TFT ION SENSOR AND TFT ION SENSOR APPARATUS USING THE SAME

CROSS-REFERENCE TO RELATED APPLICATION

This application is based upon and claims the benefit of priority from Japanese patent application No. 2014-068159, filed on Mar. 28, 2014, the disclosure of which is incorporated herein in its entirety by reference.

BACKGROUND OF THE INVENTION

1. Field of the Invention

The present invention relates to a TFT ion sensor constituted with TFT (Thin Film Transistor), a measuring method using the TFT ion sensor, and a TFT ion sensor apparatus using the TFT ion sensor.

2. Description of the Related Art

Recently, ion concentration sensors used for bio-sensing, for example, are utilized in the fields of medical services and the like. The ion concentration sensor is acquired by combining a hydrogen ion concentration detecting function on an inorganic oxide surface, an oxygen molecule identifying function on the inorganic oxide surface, and an electro-chemical device.

An ion sensitive FET (FET ion sensor) using a silicon substrate MOSFET (Metal Oxide Semiconductor Field Effect Transistor) has already been developed into a product, and it is mainly utilized as a pH (potential of hydrogen) sensor of a solution. It is electrochemically known that electric double layers are essentially formed in the interface between a solution and an insulating film. The potential difference generated in the electric double layers changes depending on pH of the solution, and it is the measuring principle thereof to sense the value of pH by reading out the change amount as Vth (threshold voltage) shift of FET.

According to the Nernst theory of electrochemistry, a potential change of about 59 mV is generated in the electric double layers in the interface of pH solution/oxide film because pH of the solution changes by "1" (the hydrogen concentration changes by one digit) at $25°$ C. That is, 59 mV/pH is the theoretical limit of the measurement sensitivity. The sensitivity of the actual ion sensitive FET products is about 45 to 50 mV/pH, and it is being studied to bring the sensitivity close to the theoretical limit.

In association with bio-medical industries, a precise sensing technique of substances in various solutions will become important for the future. In bio-sensing, a method of detecting a change in the hydrogen ion concentration at last via an enzyme reaction or the like is used often. Thus, regarding pH, a technique capable of sensing a small pH change is being required. Therefore, there has been an increasing demand for the necessity for improving the measurement sensitivity (increasing the sensitivity to be higher than 59 mV/pH) by some kind of means.

Next, documents of related techniques associated with the present invention (referred to as "related techniques" hereinafter) will be described.

Related to the TFT ion sensor utilizing Vt shift of TFT, there is a report of a case by F. Yan, et al., in which a polycrystalline silicon TFT is used ("Applied Physics Letters", vol. 86, 053901 (2005) (Non-Patent Document 1)). A silicon nitride film is used as an ion sensitive insulating film, pH sensing is performed, and the sensitivity of 54 mV/pH is acquired.

J.-C. Chou et al., performed pH sensing by using amorphous silicon TFT, and the sensitivity of 58 mV/pH was achieved ("Sensors and Actuators", B62, 92-96 (2000) (Non-Patent Document 2)).

K. Koike et al., performed pH sensing by using a transistor that used a zinc oxide that was an oxide semiconductor as a semiconductor active layer, and the sensitivity of $-20$ $\mu$A/pH was acquired ("Japanese Journal of Applied Physics", vol. 46, L865-L867 (2007) (Non-Patent Document 3)).

There is disclosed a method with which an ion sensitive insulating film is formed on an oxide semiconductor film in a bottom-gate type TFT using an oxide semiconductor, and the voltage of a reference electrode in a sensing solution is changed while a constant voltage is applied to a bottom gate electrode to perform sensing from the shift in the threshold voltage of the reference electrode voltage-drain current property (Japanese Unexamined Patent Publication 2012-73101 (Patent Document 1)).

There is disclosed a method with which an ion sensitive insulating film is formed by using a polysilazane solution in a bottom-gate type TFT having carbon nanotube as an active layer, and a top gate electrode is formed on the ion active insulating film to improve the property (Japanese Unexamined Patent Publication 2010-192599 (Patent Document 2).

There is disclosed a TFT sensor capable of performing sensing even in an ultraviolet atmosphere through cutting ultraviolet rays by a dual gate electrode of a dual-gate type TFT using an oxide semiconductor and forming an ion sensitive insulating film on the dual gate electrode (Japanese Unexamined Patent Publication 2013-76656 (Patent Document 3)).

As described above, the TFT ion sensors using the silicon semiconductor and the oxide semiconductor have been reported. All of those perform pH sensing from the shift in the property of "voltage applied to a reference electrode dipped in a sensing-target solution" with respect to "drain current".

As described above, various techniques regarding the ion sensor using TFT have been disclosed. However, disclosed in all of those documents are the methods with which the voltage of the reference electrode dipped in the sensing-target solution is changed and the ion concentration is detected from the shift of the reference voltage electrode-drain current property. With such methods, 59 mV/pH is the theoretical limit of the sensitivity in pH sensing, for example, according to the Nernst theory. The theoretical limit is constant without depending on the semiconductor material and the ion sensitive insulating film.

The pH sensor using MOSFET has already been put into practical use, and those with the sensitivity of about 55 mV/pH which is close to the theoretical limit mentioned above have been made into products. Since the actual products have been and are being made, it is considered that the sensitivity of about 55 mV/pH is sufficient when sensing the hydrogen ion concentration itself in the solvent.

Further, in a case where a bio-sensing function is implemented by providing an enzyme which solidifies only a specific substance on the ion sensitive insulating film of the TFT ion sensor, still high sensitivity is required. For example, when detecting a hormone substance existing in a neutral solution (hydrogen ion concentration: $10^{-7}$ mol/L) in concentration of about $10^{-9}$ to $10^{-8}$ mol/L based on a change in the hydrogen ion concentration, it is required to detect the change in pH of about 0.01 to 0.1 with high precision. However, according to the Nernst theory limit, it is required to detect a small property shift of about 0.59 mV to 5.9 mV. Thus, due to the influences of measurement precision fluctuation and the like, it is difficult to perform precise detection. For example, considering the influences due to the measurement precision fluctuation and the like by heat, the sensitivity is decreased further than the theoretical limit. When the so-called original signal-to-noise ratio (S/N ratio) is decreased, the noise level is included and amplified when amplification is done by an external circuit or the like. Thus, practically, the sensitivity cannot be increased.

With the related technique that is bound to the sensitivity limit according to the Nernst theory, it is difficult to detect a small amount of concentration substance such as hormone with high precision.

It is therefore an exemplary object of the present invention to provide a TFT ion sensor capable of sensing a small ion concentration change with high sensitivity.

SUMMARY OF THE INVENTION

The TFT ion sensor according to the present invention includes: a semiconductor active layer to which a source electrode and a drain electrode are connected; a gate insulating film and a gate electrode provided on one of surfaces of the semiconductor active layer; an ion sensitive insulating film provided on the other surface of the semiconductor active layer; and a reference electrode provided at a position spatially isolated from the ion sensitive insulating film, wherein: an electrostatic capacitance per unit area of the ion sensitive insulating film is larger than an electrostatic capacitance per unit area of the gate insulating film; and either a voltage detection unit for reading out a potential difference between the source electrode and the gate electrode or a current detection unit which reads out a current flown in the source electrode or the drain electrode is provided further.

DETAILED DESCRIPTION OF THE PREFERRED EMBODIMENTS

Figure 1:
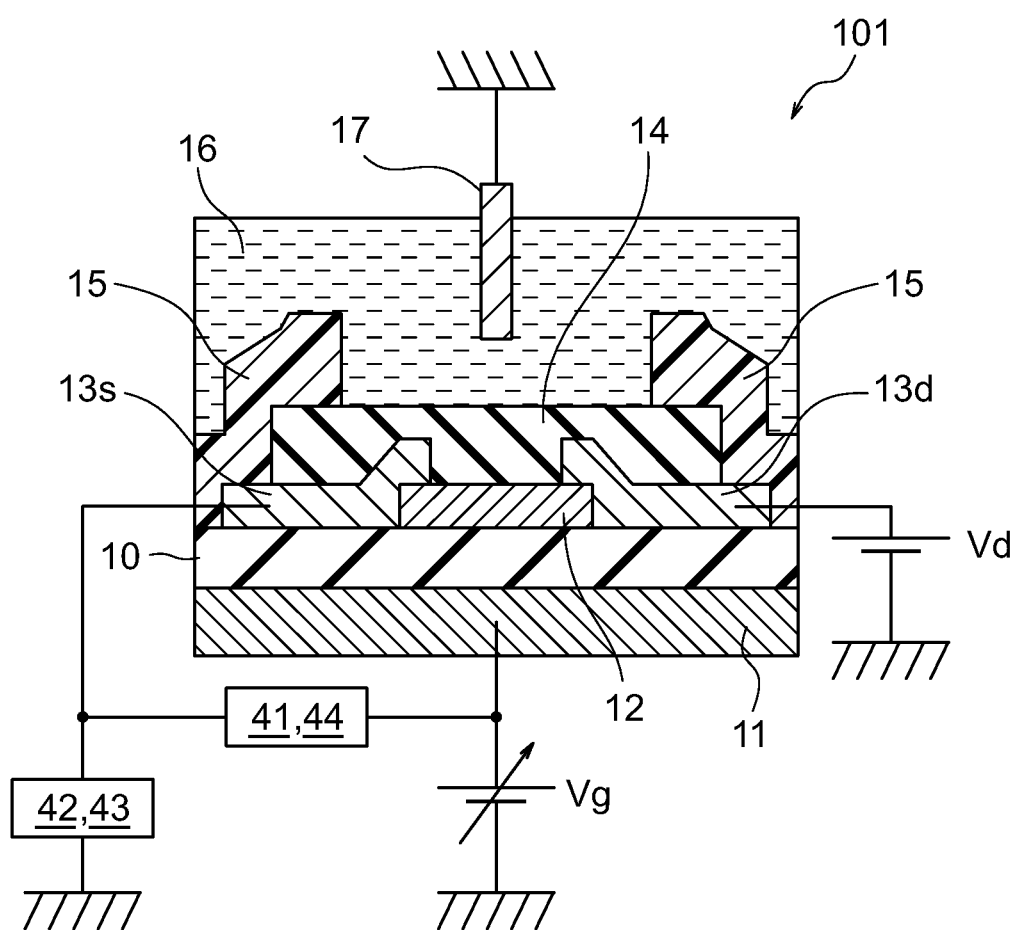
FIG. 1 is a sectional view showing a TFT ion sensor of a first exemplary embodiment and Example 1.

A first TFT ion sensor of the present invention includes an island shaped semiconductor active layer to which a source electrode and a drain electrode are connected. A gate insulating film and a gate electrode are formed on one of the surfaces of the semiconductor active layer, an ion sensitive insulating film is formed on the other surface of the semiconductor active layer, and a reference electrode is provided at a position spatially isolated from the ion sensitive insulating film. In the TFT ion sensor, an electrostatic capacitance per unit area of the ion sensitive insulating film is larger than an electrostatic capacitance per unit area of the gate insulating film, and the TFT ion sensor further includes a mechanism for reading out a potential difference between the source electrode and the gate electrode.

Further, a second TFT ion sensor of the present invention includes an island shaped semiconductor active layer to which a source electrode and a drain electrode are connected. A gate insulating film and a gate electrode are formed on one of the surfaces of the semiconductor active layer, an ion sensitive insulating film is formed on the other surface of the semiconductor active layer, and a reference electrode is provided at a position spatially isolated from the ion sensitive insulating film. In the TFT ion sensor, an electrostatic capacitance per unit area of the ion sensitive insulating film is larger than an electrostatic capacitance per unit area of the gate insulating film, and the TFT ion sensor further includes a mechanism for reading out a current value flown between the source electrode and the drain electrode.

Furthermore, a third TFT ion sensor of the present invention includes an island shaped semiconductor active layer to which a source electrode and a drain electrode are connected. A gate insulating film and a gate electrode are formed on one of the surfaces of the semiconductor active layer, an ion sensitive insulating film is formed on the other surface of the semiconductor active layer, and a reference electrode is provided at a position spatially isolated from the ion sensitive insulating film. In the TFT ion sensor, an electrostatic capacitance per unit area of the ion sensitive insulating film is larger than an electrostatic capacitance per unit area of the gate insulating film, and the TFT ion sensor further includes a mechanism for detecting the ion concentration in the sensing-target substance from the shift amount in the curve that shows the relation between the potential difference between the gate electrode and the source electrode and the current flown between the drain electrode and the source electrode when the sensing-target substance is placed on the ion sensitive insulating film.

That is, unlike the case of the related techniques which detect the ion concentration from the shift in the reference electrode voltage-drain current property, the present invention detects the ion concentration from the shift in the gate electrode voltage-drain current property.

Such TFT ion sensor includes a mechanism which reads out a potential difference that is acquired by multiplying a value of the ratio acquired by dividing an electrostatic capacitance per unit area of the ion sensitive insulating film by an electrostatic capacitance per unit area of the gate insulating film to the potential difference generated between the ion sensitive insulating film and the sensing-target substance (corresponding to the electric double layer voltage generated in the interface) when the sensing-target substance is placed on the ion sensitive insulating film.

As described above, the maximum value of the change in the electric double layer voltage with respect to the change in the hydrogen ion concentration is 59 mV/pH. However, with the present invention, the value of the ratio acquired by dividing the electrostatic capacitance per unit area of the ion sensitive insulating film by the electrostatic capacitance per unit area of the gate insulating film is larger than 1. Thus, it is possible to achieve the sensitivity that is higher than 59 mV/pH.

Such highly sensitive TFT ion sensor is the sensor that is characterized to include a mechanism which can control the potential difference between the gate electrode and the source electrode so that a constant current flows between the source electrode and the drain electrode or the sensor that is characterized to include a mechanism which can control the current flown between the drain electrode and the source electrode so that the potential difference between the gate electrode and the source electrode becomes constant.

Unlike the related techniques, the present invention executes ion concentration sensing based on the shift in the property of the drain current not with respect the reference voltage but with respect to the voltage applied to the gate electrode. In a case of using such detection method, detection with higher sensitivity than the Nernst limit can be done theoretically through making the electrostatic capacitance per unit area of the ion sensitive insulating film larger than the electrostatic capacitance per unit area of the gate insulating film. The effect of the present invention does not deny the Nernst theory by any means. It is the result achieved when the electric double layer potential difference generated on the surface of the ion sensitive insulating film according to the Nernst theory is "amplified" through the mutual effect of the bottom gate electric field and the top gate electric field. The amplification effect is achieved by making the electrostatic capacitance per unit area of the ion sensitive insulating film larger than the electrostatic capacitance per unit area of the gate insulating film. This effect does not depend on the amplification by the external circuit and can achieve the original high sensitivity of the sensor itself without being influenced by various kinds of fluctuations. Therefore, the issues of the related techniques can be overcome.

Hereinafter, modes (referred to as "exemplary embodiments" hereinafter) for embodying the present invention will be described by referring to the accompanying drawings. Note that same reference numerals are used for substantially same structural elements in the current Specification and the drawings. The shapes in the drawings are illustrated in a manner to be easily comprehended by those skilled in the art, so that sizes and ratios thereof are not necessarily consistent with the actual ones.

First Exemplary Embodiment

FIG. 1 is a sectional view showing a TFT ion sensor 101 according to a first exemplary embodiment.

The TFT ion sensor 101 includes: a semiconductor active layer 12 in which a source electrode 13s and a drain electrode 13d are connected; a thermal oxide film 10 as a gate insulating film and a silicon substrate 11 as a gate electrode provided on one of the surfaces of the semiconductor active layer 12; an ion sensitive insulating film 14 provided on the other surface of the semiconductor active layer 12; and a reference electrode 17 provided at a position spatially isolated from the ion sensitive insulating film 14, in which the electrostatic capacitance per unit area of the ion sensitive insulating film 14 is larger than the electrostatic capacitance per unit area of the gate insulating film (the thermal oxide film 10). Further, the TFT ion sensor 101 further includes either a voltage detection unit 41 which reads out the potential difference between the source electrode 13s and the gate electrode (the silicon substrate 11) or a current detection unit 42 which reads out the current flown in the source electrode 13s or the drain electrode 13d.

In a case where the voltage detection unit 41 is provided, a voltage control unit 43 which controls the potential difference between the source electrode 13s and the gate electrode (the silicon substrate 11) so that the constant current flows between the source electrode 13s and the drain electrode 13d may be provided further. An example of the measuring method of that case is as follows. That is, the space between the ion sensitive insulating film 14 and the reference electrode 17 is filled with a sensing-target substance 16, the potential difference between the source electrode 13s and the gate electrode (the silicon substrate 11) is controlled so that a constant current flows between the source electrode 13s and the drain electrode 13d, and the potential difference between the source electrode 13s and the gate electrode (the silicon substrate 11) is read out.

In a case where the current detection unit 42 is provided, a current control unit 44 which controls the current flown between the source electrode 13s and the drain electrode 13d so that the potential difference between the gate electrode (the silicon substrate 11) and the source electrode 13s becomes constant may be provided further. An example of the measuring method of that case is as follows. That is, the space between the ion sensitive insulating film 14 and the reference electrode 17 is filled with a sensing-target substance 16, the current flown between the source electrode 13s and the drain electrode 13d is controlled so that the potential difference between the gate electrode (the silicon substrate 11) and the source electrode 13s becomes constant, and the current flown between the source electrode 13s and the drain electrode 13d is read out.

The potential difference between the source electrode 13s and the gate electrode (the silicon substrate 11) is a potential difference acquired by multiplying a ratio that is acquired by dividing the electrostatic capacitance per unit area of the ion sensitive insulating film 14 by the electrostatic capacitance per unit area of the gate insulating film (the thermal oxide film 10) to the potential difference generated between the ion sensitive insulating film 14 and the sensing-target substance 16 when the sensing-target substance 16 is placed on the ion sensitive insulating film 14.

A gate voltage Vg is applied to the gate electrode (the silicon substrate 11), and a drain voltage Vd is applied to the drain electrode 13d. For example, the voltage detection unit 41 is a voltmeter, the current detection unit 42 is an ammeter, the voltage control unit 43 is a constant-current source, and the current control unit 44 is a constant-voltage source.

The TFT ion sensor 101 will be described in more details. The semiconductor active layer 12 in an island shape is formed on the silicon substrate 11 where the thermal oxide film 10 is formed, and the source electrode 13s and the drain electrode 13d are formed to be in contact with a part of the top surface of the semiconductor active layer 12. The ion sensitive insulating film 14 is formed on the semiconductor active layer 12 the source electrode 13s, and the drain electrode 13d. In the first exemplary embodiment, the silicon substrate 11 functions as the gate electrode, and the thermal oxide film 10 functions as the gate insulating film, respectively. Only the ion sensitive insulating film 14 in a region corresponding to the channel part of the TFT is exposed, and the other region is covered by a protection insulating film 15. The TFT of such structure is disposed within the sensing-target substance 16, and the reference electrode 17 is provided in the sensing-target substance 16.

It is the point of the first exemplary embodiment to make the electrostatic capacitance per unit area of the ion sensitive insulating film 14 larger than the electrostatic capacitance per unit area of the gate insulating film (the thermal oxide film 10) in the TFT ion sensor 101 having the above-described structures, and to detect the change in the ion concentration in the sensing-target substance 16 from the change in the threshold voltage regarding the property of the gate-source voltage with respect to the source-drain current (abbreviated as "Vg-Id property" hereinafter).

Example 1

Next, Example 1 which is a more concrete form of the first exemplary embodiment will be described by referring to FIG. 1.

First, the silicon substrate 11 on which the thermal oxide film 10 having a thickness of 200 nm was prepared. Instead of the thermal oxide film 10, a silicon oxide film, a silicon nitride film, or the like deposited by a plasma CVD (Chemical Vapor Deposition) method or a sputtering method may also be used.

Further, an oxide semiconductor film having a thickness of 50 nm constituted with In—Ga—Zn—O was deposited by the sputtering method by using a metal mask on the silicon substrate 11 on which the thermal oxide film 10 was formed. At that time, a sinter target constituted with In—Ga—Zn—O was used, the substrate was not heated, and a DC (Direct Current) sputtering method was employed in a mixed gas atmosphere of an argon gas and an oxygen gas. After the deposition, annealing was performed at 400° C. for an hour. Through patterning the oxide semiconductor film, the island shaped semiconductor active layer 12 was formed.

Subsequently, the source electrode 13s and the drain electrode 13d were formed by performing DC sputtering of a molybdenum metal by using a metal mask. The film thickness of the source electrode 13s and the drain electrode 13d is 30 nm.

Further, the ion sensitive insulating film 14 having a thickness of 200 nm constituted with tantalum oxide was deposited by the sputtering method by using a metal mask. At that time, a sinter target constituted with Ta—O was used, the substrate was not heated, and an RF (Radio Frequency) sputtering method was employed in a mixed gas atmosphere of an argon gas and an oxygen gas. Thereafter, annealing was performed at 300° C. for an hour. The relative dielectric constant of the thermal oxide film was about 4, and the relative dielectric constant of the tantalum oxide deposited by sputtering was about 20. The film thickness was 200 nm for the both, so that the difference in the relative dielectric constant values was reflected. Thus, the electrostatic capacitance per unit area of the ion sensitive insulating film 14 constituted with the tantalum oxide was about five times larger than the electrostatic capacitance per unit area of the gate insulating film constituted with the thermal oxide film 10.

Thereafter, formed was a structure in which an epoxy resin was used as the protection insulating film 15, the surface of the ion sensitive insulating film 14 on the channel region of the semiconductor active layer 12 was exposed, and the other region was covered by the epoxy resin.

The TFT having the above-described structures was dipped in a MacIlvaine buffer solution that is the sensing-target substance 16, and the reference electrode 17 formed with platinum was placed in the MacIlvaine buffer solution. The MacIlvaine buffer solution is constituted with a mixed solution of citric acid of 0.025 mol/L and potassium hydrogen phosphate of 0.05 mol/L. The hydrogen ion concentration (pH) as the sensing target was changed by the mixture ratio in a range of 3 to 8.

Figure 2:
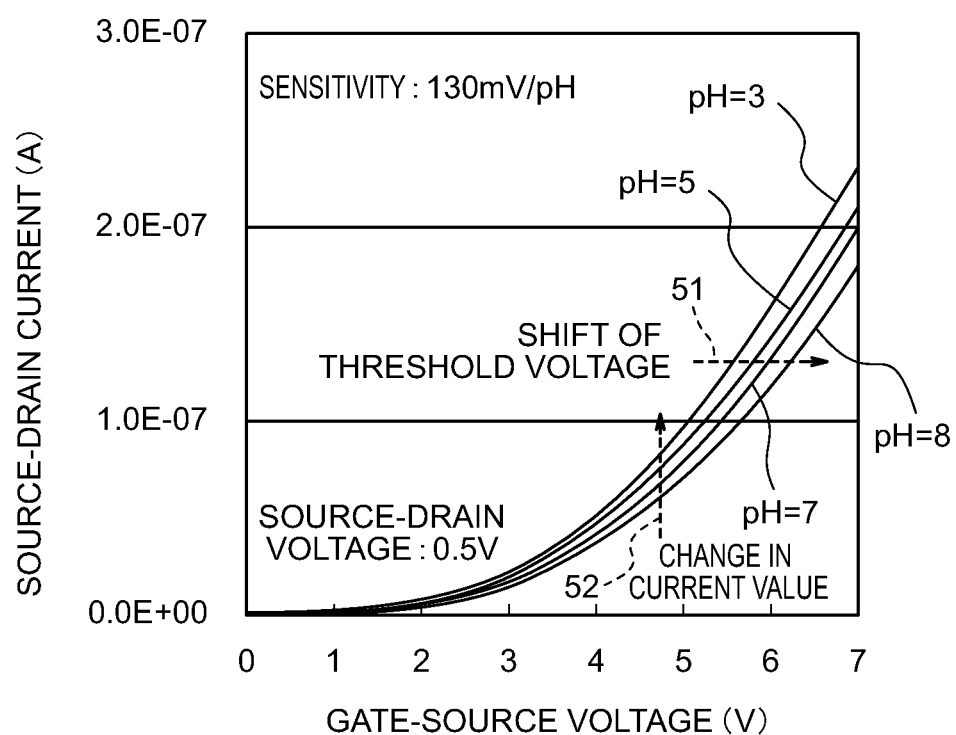
FIG. 2 is a graph showing a gate-source voltage with respect to a source-drain current, which is a measurement result of pH sensing according to Example 1.

A constant voltage of 0.5 V was applied to the drain electrode 13d of the TFT ion sensor 101 having the above-described structures, and the source electrode 13s and the reference electrode 17 were set to the ground potential (0 V). The gate voltage Vg was changed in a range of −2 V to +7 V in such biased state to measure the Vg-Id property in the buffer solution of each pH at a room temperature. FIG. 2 shows the Vg-Id property measured in the buffer solution with each value of pH=3, 5, 7, 8.

As can be seen from FIG. 2, the Vg-Id property is shifted to the positive direction as the value of pH becomes higher. When the gate-source voltage to which the constant current value of $1 \times 10^{-7}$ A was applied as the source-drain current was read out by each pH (right-pointing broken-line arrow 51), the shift amount per unit pH, i.e., the sensitivity, was about 130 mV/pH. This is twice or more of the theoretical limit 59 mV/pH as in the cases of the related techniques determined by the Nernst formula. Thereby, the effect of the first exemplary embodiment was confirmed.

The point to notice herein is that the result of the first exemplary embodiment does not conflict with the Nernst theory by any means. It can be said that the result is acquired when the electric double layer potential difference (this potential difference is ought to be 59 mV/pH or less according to the theory) generated on the surface of the tantalum oxide according to the Nernst theory is amplified through the mutual effect and the capacitance difference of the bottom gate electric field and the top gate electric field.

Inversely speaking, the contrivance for generating such amplification effect is originated from the point of the first exemplary embodiment. The point of the first exemplary embodiment is that the electrostatic capacitance of the ion sensitive insulating film 14 is larger than the electrostatic capacitance of the gate insulating film (the thermal oxide film 10) and that the change in the ion concentration in the sensing-target substance 16 can be detected from the change in the threshold voltage of the Vg-Id property.

In Example 1, a case of $1 \times 10^{-7}$ A as a constant source-drain current value is described. However, the value of the constant current is not limited only to that and it can be set arbitrarily according to the size of the TFT or the current value that can be easily detected. Further, while a case of supplying the constant potential difference of 0.5 V between the source electrode 13s and the drain electrode 13d is described above, it is not limited to such value. The potential difference can be arbitrarily set according to the size of the TFT and as a difference with which the current value that can be detected easily can be acquired.

In the above, the measuring method for detecting the change in the ion concentration within the sensing-target substance 16 from the change in the threshold voltage of the Vg-Id property is described. However, it is also possible to read out the source-drain current value at the time of a specific gate-source voltage by an ammeter and to detect the change in the ion concentration from that change. An example of such sensing concept is shown by an upward broken-line arrow 52 in FIG. 2. As shown in FIG. 2, the shift amount in the Vg-Id property by the change in the pH value in the first exemplary embodiment is large compared to the cases of the related techniques, so that the change in the current value in the direction of the upward broken-line arrow 52 becomes larger as well. This shows that the sensitivity of pH sensing becomes higher. Thus, through reading out the pH value from the current value by employing the first exemplary embodiment, the TFT ion sensor with the higher sensitivity than those of the related techniques can be achieved.

Here, the case of using the oxide semiconductor as the semiconductor active layer 12 is described. The oxide semiconductor such as In—Ga—Zn—O accumulates almost no holes (positive holes) in the semiconductor, so that a depletion state (a state where carriers hardly exist in the semiconductor) can be achieved easily. In such depletion state, the mutual effect of the bottom-gate electric field and the top-gate electric field becomes more prominent, so that the above-described amplification effect, i.e., the high sensitivity, can be acquired more effectively. Therefore, in the first exemplary embodiment, it is important to use the semiconductor active layer 12 where holes are hardly accumulated. As an example thereof, the oxide semiconductor is employed.

While the ion sensitive insulating film 14 is not limited to the tantalum oxide, it is desirable to use a material with a high relative dielectric constant. For example, other than tantalum oxide, hafnium oxide, aluminum oxide, barium titanate, strontium titanate, a silicon nitride film, or the like may be used. Also, a laminated layer of any of those may be used as well. Further, the gate insulating film is not limited to the silicon oxide. Silicon nitride, aluminum oxide, or the like may be used or a laminated film of any of those may be used as well.

Further, the potential of the reference electrode 17 at the time of measurement is not limited to the ground potential but may be set arbitrarily in accordance with the original transistor property (the property in the air before being placed in the sensing-target substance 16). For example, in a case where the original transistor property is shifted to the positive direction, and a sufficient drain current value cannot be acquired, it is also possible to perform detection in a state where a sufficient current value is acquired through shifting the transistor property to the negative direction by supplying a proper positive potential to the reference electrode 17 with respect to the source electrode 13s. Inversely, in a case where the original transistor property is shifted to the negative direction and the current value is too high, the current value can be limited to a proper value through performing detection while supplying a proper negative potential to the reference electrode 17. Further, as the reference electrode 17, it is also possible to use Ag/AgCl.

It is also possible to use a highly heat-resistant metal such as tungsten for the source electrode 13s and the drain electrode 13d and to perform annealing at a high temperature of 500° C. or higher after forming the ion sensitive insulating film 14. Such high-temperature annealing makes it possible to improve the film quality of the ion sensitive insulating film 14 for improving the sensing sensitivity further. At the same time, the ion sensitive insulating film 14 is formed more minute, so that it is possible to suppress short-circuit generated when the sensing-target substance (solvent) 16 penetrates into the ion sensitive insulating film 14 and reaches the semiconductor active layer 12, for example.

As an exemplary advantage according to the invention, the present invention makes it possible to amplify and detect the electric double layer potential difference generated on the surface of the ion sensitive insulating film (the potential difference generated according to the Nernst theory), so that it is possible to achieve the TFT ion sensor capable of sensing a small ion concentration change with high sensitivity. By actively utilizing that effect, it becomes possible to achieve high sensitivity in bio-sensing which converts enzyme reactions and antigen-antibody reactions to electric signals.

Second Exemplary Embodiment

Figure 3:
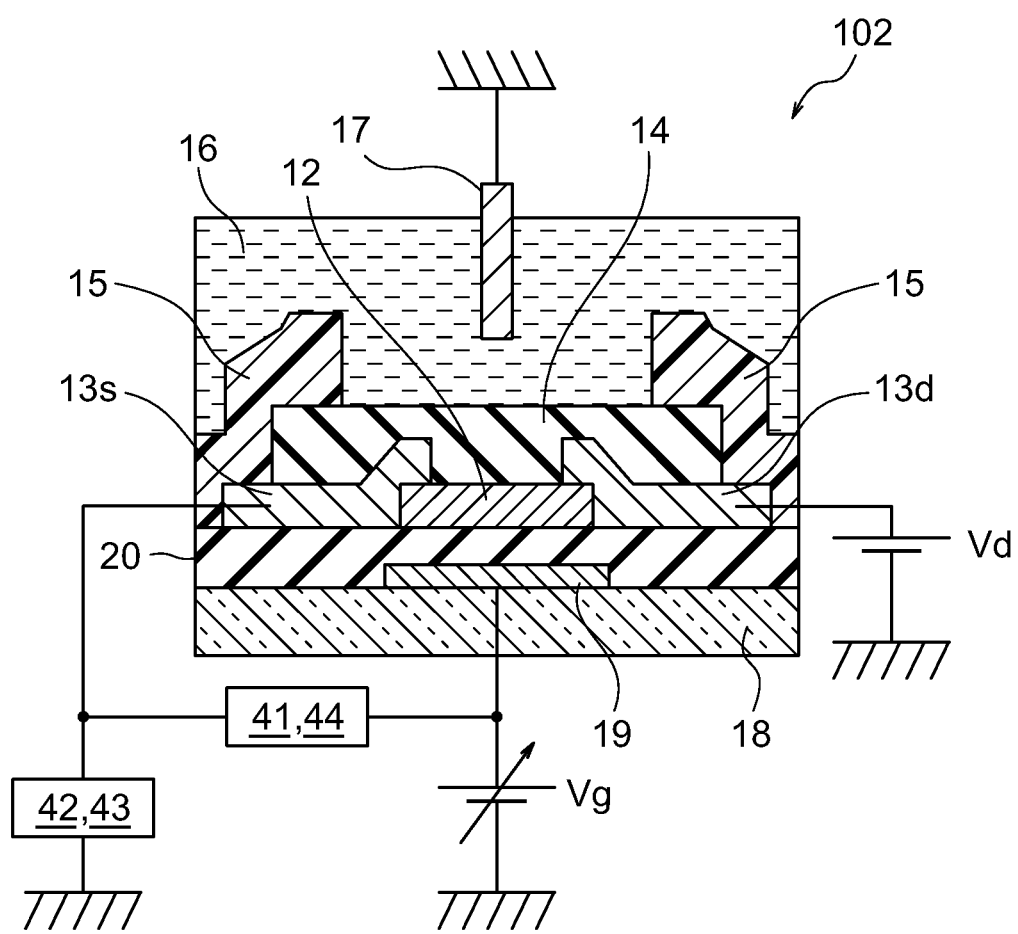
FIG. 3 is a sectional view showing a TFT ion sensor of a second exemplary embodiment and Example 2.

FIG. 3 is a sectional view showing a TFT ion sensor 102 according to a second exemplary embodiment.

A gate electrode 19 is formed on a glass substrate 18, and a gate insulating film 20 is formed further. An island shaped semiconductor active layer 12 is formed on the gate insulating film 20, and a source electrode 13s and a drain electrode 13d are formed to be in contact with a part of the top surface of the semiconductor active layer 12. An ion sensitive insulating film 14 is formed on the semiconductor active layer 12, the source electrode 13s, and the drain electrode 13d. Only the ion sensitive insulating film 14 in a region corresponding to the channel part of the semiconductor active layer 12 is exposed, and the other region is covered by a protection insulating film 15. The TFT of such structure is disposed within the sensing-target substance 16, and a reference electrode 17 is provided in the sensing-target substance 16.

It is the point of the second exemplary embodiment to make the electrostatic capacitance per unit area of the ion sensitive insulating film 14 larger than the electrostatic capacitance per unit area of the gate insulating film 20 in the TFT ion sensor 102 having the above-described structures, and to detect the change in the ion concentration in the sensing-target substance 16 from the change in the threshold voltage of the Vg-Id property. Other structures, operations, and effects of the second exemplary embodiment are the same as those of the first exemplary embodiment.

Example 2

Next, Example 2 which is a more concrete form of the second exemplary embodiment will be described by referring to FIG. 3.

An alloy material having aluminum as the main component was deposited on the glass substrate 18 by sputtering, and the gate electrode 19 was formed by using a photolithography process constituted with application of resist, exposure, development, etching, and exfoliation of the resist.

Thereon, a silicon oxide film having a thickness of 300 nm was deposited at a substrate temperature of 350° C. by using a plasma CVD method to form the gate insulating film 20.

Subsequently, an oxide semiconductor film constituted with In—Ga—Zn—O was deposited to have a thickness of 30 nm by a sputtering method, and it was patterned to a prescribed island shape by a photolithography process to form the semiconductor active layer 12. After the patterning, annealing processing was performed in the air at 400° C. for one hour.

Then, a titanium metal was deposited by sputtering, and the titanium metal was etched by using a fluorine-gas based plasma (e.g., $CF_4$ or $SF_6$) after patterning the photoresist to form the source electrode 13s and the drain electrode 13d in prescribed shapes. At that time, the In—Ga—Zn—O film is not etched by the fluorine-based plasma, so that it is not excessively etched at the time of etching the titanium metal.

Thereafter, an aluminum oxide film having a thickness of 200 nm was deposited as the ion sensitive insulating film 14 by a sputtering method using a metal mask, and annealing processing was performed in the air at 400° C. for one hour.

The relative dielectric constant of the aluminum oxide film is about 8 whereas the relative dielectric constant of the silicon oxide film is 4. Thus, the electrostatic capacitance per unit area of the ion sensitive insulating film 14 formed with aluminum oxide is larger than the electrostatic capacitance per unit area of the gate insulating film 20 formed with the silicon oxide film.

Then, formed was a structure in which an epoxy resin was used as the protection insulating film 15, the surface of the ion sensitive insulating film 14 on the channel region of the semiconductor active layer 12 was exposed, and the other region was covered by the epoxy resin.

The TFT having the above-described structures was dipped in a MacIlvaine buffer solution that is the sensing-target substance 16, and the reference electrode 17 formed with platinum was placed in the MacIlvaine buffer solution.

1 V was applied to the drain electrode 13d of the TFT ion sensor 102 having the above-described structures, and the ground potential of the source electrode 13s and the reference electrode 17 were set to the ground potential (0 V). Further, the Vg-Id property of the TFT in the air was shifted to the positive side, so that 2 V was supplied to the reference electrode 17 for acquiring a proper drain current value. The gate voltage was changed in a range of −5 V to +10 V in such biased state, and the Vg-Id property in the buffer solution of each pH was measured at a room temperature. As a result, the sensing sensitivity higher than 59 mV/pH as the theoretical limit that is determined from the Nernst formula was acquired.

In Examples 1 and 2 described above, the ion sensitive insulating film 14 was deposited to be in contact with the top surface of the semiconductor active layer 12 after forming the semiconductor active layer 12, the source electrode 13s, and the drain electrode 13d. Among the semiconductor materials, there is a type with which defects tend to be formed in the interface when the ion sensitive insulating film 14 with a high dielectric constant is directly deposited thereon. In such case, it is possible to deposit an insulating film with which a fault density becomes smaller after forming the semiconductor active layer 12, the source electrode 13s, and the drain electrode 13d, and depositing the ion sensitive insulating film 14 thereon. With that, the sensitivity can be increased further.

For example, after depositing a silicon oxide film to be in contact with the top surface of the In—Ga—Zn—O film or the silicon semiconductor film, tantalum oxide may be deposited thereon as the ion sensitive insulating film 14. In that case, it is necessary to make the electrostatic capacitance constituted with a laminated film of the silicon oxide film and the tantalum oxide film larger than the electrostatic capacitance of the gate insulating film.

(Example 3) Etch-Stop Type IGZO-TFT

Figure 4:
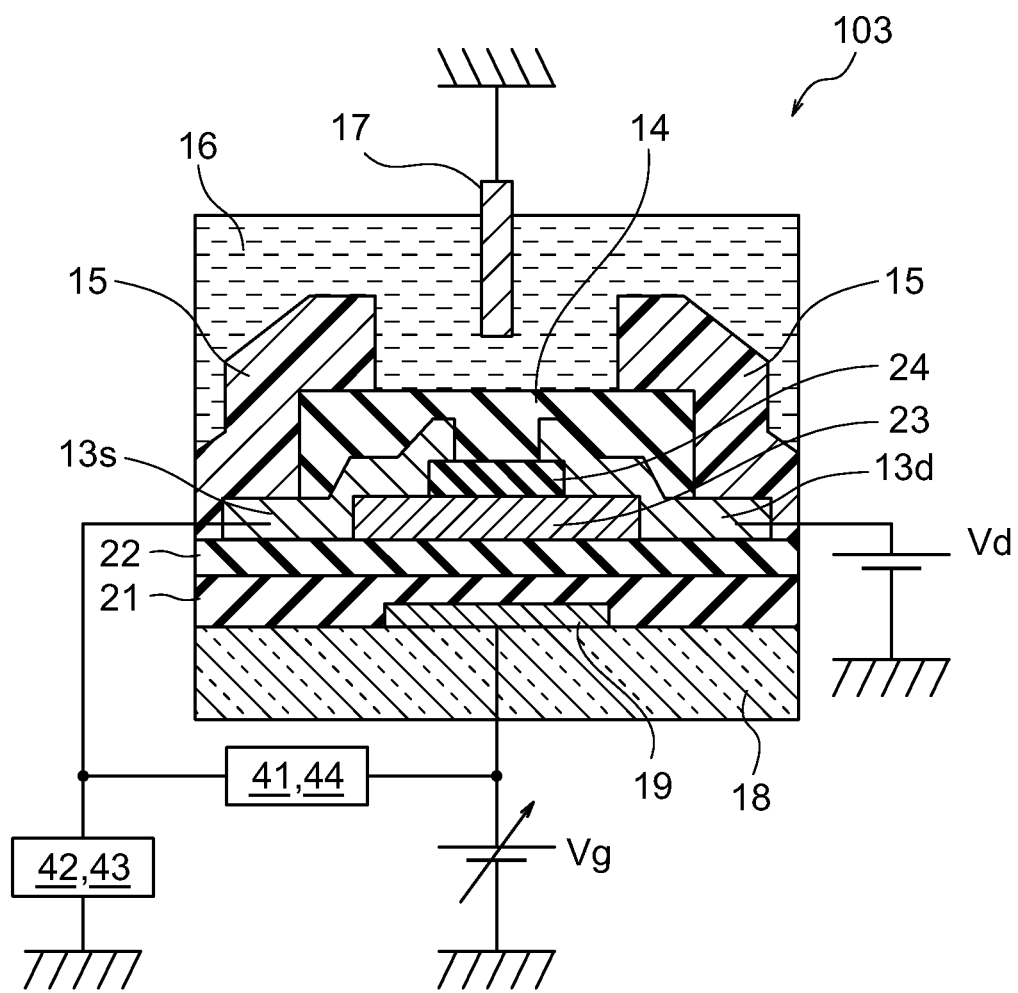
FIG. 4 is a sectional view showing a TFT ion sensor of Example 3.

FIG. 4 is a sectional view showing a TFT ion sensor 103 of Example 3. Example 3 that is a modification example of the second exemplary embodiment will be described by referring to FIG. 4.

An alloy material having molybdenum as the main component was deposited on the glass substrate 18 by sputtering, and the gate electrode 19 was formed by using a photolithography process constituted with application of resist, exposure, development, etching, and exfoliation of the resist.

Thereon, a silicon nitride film 21 having a thickness of 200 nm was deposited thereon and a silicon oxide film 22 having a thickness of 100 nm was deposited successively at a substrate temperature of 350° C. by using a plasma CVD method, and 300 nm of a laminate film thereof was used as the gate insulating film.

Subsequently, an oxide semiconductor film 23 constituted with In—Sn—Zn—O was deposited to have a thickness of 50 nm by a sputtering method as the semiconductor active layer, and it was patterned to a desired island shape by a photolithography process. After the patterning, annealing processing was performed in the air at 400° C. for one hour.

Then, a silicon oxide film having a thickness of 50 nm was deposited by a plasma CVD method, and an etch-stop film 24 in a desired shape was formed by a photolithography process.

Further, a molybdenum metal was deposited by sputtering, and the molybdenum metal was etched by using a phosphoric-acid based solution after patterning the resist to form the source electrode 13s and the drain electrode 13d in desired shapes.

Thereafter, a strontium titanate film having a thickness of 200 nm was deposited by a sputtering method using a metal mask, and annealing processing was performed in the air at 400° C. for one hour to form the ion sensitive insulating film 14. The relative dielectric constant of the strontium titanate film is about 50 whereas the relative dielectric constant of the silicon nitride film and the silicon oxide film is 7 to 4. Thus, the electrostatic capacitance per unit area of the laminated film of the strontium titanate film as the ion sensitive insulating film 14 and the silicon oxide film as the etch-stop film 24 is larger than the electrostatic capacitance per unit area of the gate insulating film constituted with the laminated film of the silicon oxide film 22 and the silicon nitride film 21.

Then, formed was a structure in which an acryl resin was used as the protection insulating film 15, the surface of the ion sensitive insulating film 14 on the channel region of the oxide semiconductor film 23 was exposed, and the other region was covered by the acryl resin.

The TFT having the above-described structures was dipped in a MacIlvaine buffer solution that is the sensing-target substance 16, and the reference electrode 17 constituted with silver/silver chloride was placed in the MacIlvaine buffer solution.

1.5 V was applied to the drain electrode 13d of the TFT ion sensor 103 having the above-described structures, and the source electrode 13s and the reference electrode 17 were set to the ground potential (0 V). Further, the Vg-Id property of the TFT in the air was shifted to the negative side, so that −3 V was supplied to the reference electrode 17 for acquiring a proper drain current value. The gate voltage Vg was changed in a range of −7 V to +8 V in such biased state, and the Vg-Id property in the buffer solution of each pH was measured at a room temperature. As a result, the sensing sensitivity higher than 59 mV/pH as the theoretical limit that is determined from the Nernst formula was acquired.

In Examples 2 and 3 above, the case of using the oxide semiconductor as the island shaped semiconductor active layer is described. However, when using the oxide semiconductor, it is also possible to use aluminum oxide as the gate insulating film. In a case of using the aluminum oxide as the gate insulating film, the defect density of oxygen defect or the like in the interface between the gate insulating film and the oxide semiconductor becomes small compared to the case of using the silicon oxide or the silicon nitride. Therefore, it is possible to achieve the more sophisticated TFT ion sensor.

Further, as the island shaped semiconductor active layer, it is also possible to use amorphous silicon hydride. In such case, the detection drain current value may be increased by improving the ohmic contact property through inserting n-type amorphous silicon hydride acquired by doping phosphor as impurity between the amorphous silicon hydride film and the source-drain electrode. Further, not only inorganic substances such as the oxide semiconductor and the amorphous silicon hydride but also a semiconductor active layer constituted with an organic substance such as pentacene may be used.

(Example 4) Polysilicon-TFT

Figure 5:
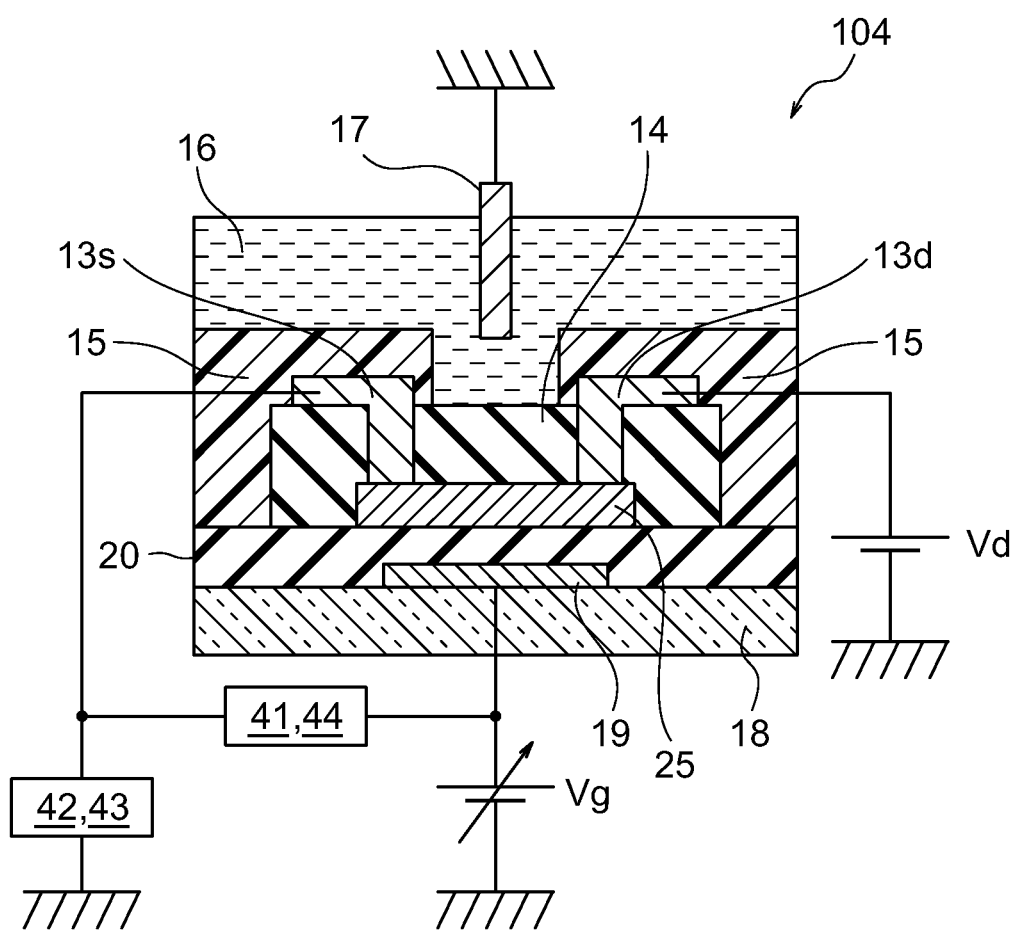
FIG. 5 is a sectional view showing a TFT ion sensor of Example 4.

FIG. 5 is a sectional view showing a TFT ion sensor 104 of Example 4. Example 4 that is a modification example of the second exemplary embodiment will be described by referring to FIG. 5.

An alloy material having tungsten as the main component was deposited on the glass substrate 18 by sputtering, and the gate electrode 19 was formed by using a photolithography process constituted with application of resist, exposure, development, etching, and exfoliation of the resist.

Thereon, a silicon oxide film having a thickness of 200 nm was deposited thereon at a substrate temperature of 350° C. by using a plasma CVD method, and it was used as the gate insulating film 20.

Subsequently, an amorphous silicon hydride film having a thickness of 50 nm was deposited by a plasma CVD method. After performing dehydrogenation processing to eliminate hydrogen in the amorphous silicon hydride film by annealing at 400° C., an excimer laser was irradiated to the dehydrogenated amorphous silicon hydride film to form a polycrystalline silicon film. Through patterning the polycrystalline silicon film into a desired island shape, a polycrystalline silicon film 25 was formed. Subsequently, boron was introduced to a part to be the source-drain region of the polycrystalline silicon film 25 to make it into a p-type region. Needless to say, an n-type source-drain region may be formed by introducing phosphor into that part.

Thereafter, a tantalum oxide film having a thickness of 200 nm was deposited by a sputtering method using a metal mask, and annealing processing was performed in the air at 400° C. for one hour to form the ion sensitive insulating film 14. The relative dielectric constant of the tantalum oxide film is about 20 whereas the relative dielectric constant of the silicon oxide film is 4. Thus, the electrostatic capacitance per unit area of the tantalum oxide film as the ion sensitive insulating film 14 is larger than the electrostatic capacitance per unit area of the gate insulating film 20 that is formed with a silicon oxide film.

A contact hole was formed in the tantalum oxide film corresponding to the source-drain region. Thereafter, molybdenum was deposited by sputtering. Through patterning the molybdenum film into a desired shape, the source electrode 13$s$ and the drain electrode 13$d$ connected to the source-drain region, respectively, were formed.

Then, formed was a structure in which an epoxy resin was used as the protection insulating film 15, the surface of the ion sensitive insulating film 14 on the channel region of the polycrystalline silicon film 25 was exposed, and the other region was covered by the epoxy resin.

The polycrystalline silicon TFT having the above-described structures was dipped in a MacIlvaine buffer solution that is the sensing-target substance 16, and the reference electrode 17 constituted with platinum was placed in the MacIlvaine buffer solution.

0.5 V was applied to the drain electrode 13$d$ of the TFT ion sensor 104 having the above-described structures, and the source electrode 13$s$ and the reference electrode 17 were set to the ground potential (0 V). Further, the gate voltage was changed in a range of −2 V to +7 V in such biased state, and the Vg-Id property in the buffer solution of each pH was measured at a room temperature. As a result, the sensing sensitivity higher than 59 mV/pH as the theoretical limit that is determined from the Nernst formula was acquired.

Third Exemplary Embodiment

Figure 6A:
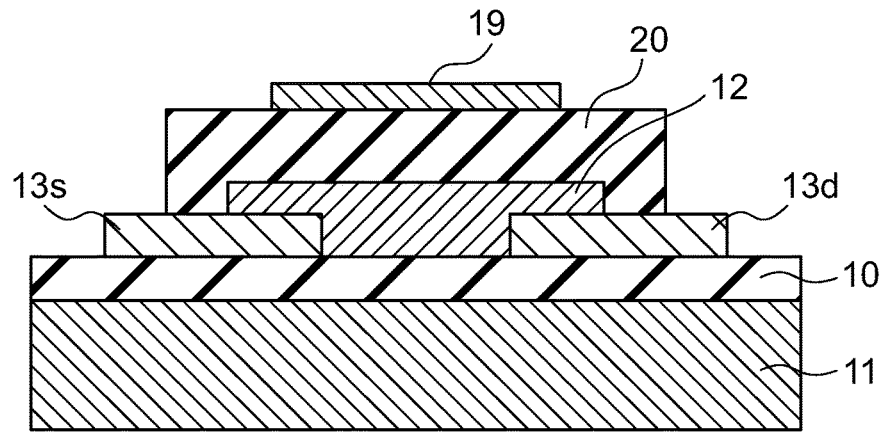
FIGS. 6A and 6B are sectional views showing a TFT ion sensor of a third exemplary embodiment and Example 5.
Figure 6B:
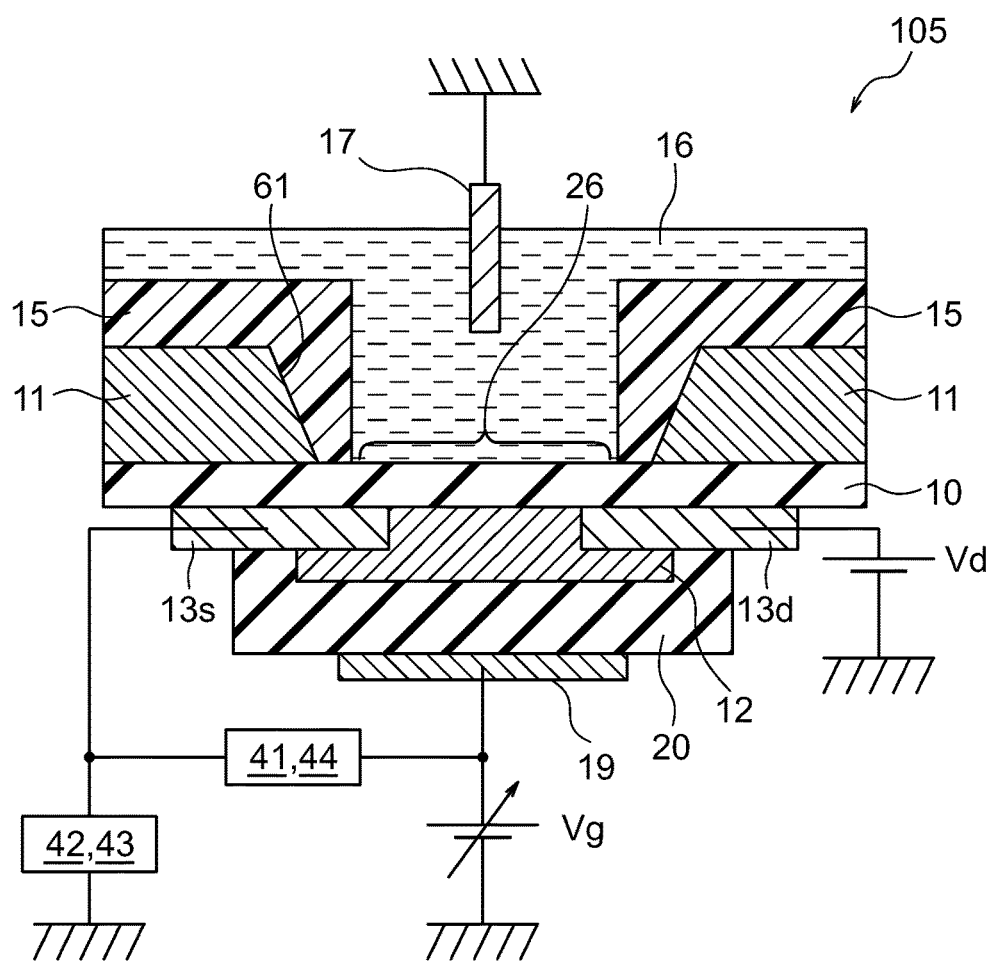

FIGS. 6A and 6B are sectional views showing a TFT ion sensor 105 according to a third exemplary embodiment.

As shown in FIG. 6A, a source electrode 13$s$, a drain electrode 13$d$, an island shaped semiconductor active layer 12, a gate insulating film 20, and a gate electrode 19 are formed in this order on a silicon substrate 11 where a thermal oxide film 10 is formed.

Further, as shown in FIG. 6B, an opening part 61 is provided in the silicon substrate 11 so that a thermal oxide film 26 located under the semiconductor active layer 12 is exposed. Through removing the part of the silicon substrate 11, which is located under the semiconductor active layer 12, the thermal oxide film 26 located under the semiconductor active layer 12 is exposed. The exposed thermal oxide film 26 functions as the ion sensitive insulating film. Further, the thermal oxide film 26 part out of the thermal oxide film 10 is exposed, and the other part is covered by a protection insulating film 15. The TFT having such structures is placed in a sensing-target substance 16, and a reference electrode 17 is provided in the sensing-target substance 16.

The electrostatic capacitance per unit area of the ion sensitive insulating film (the thermal oxide film 26) is larger than the electrostatic capacitance per unit area of the gate insulating film 20 in the TFT ion sensor 105 having the above-described structures, and the change in the ion concentration in the sensing-target substance 16 is detected from the change in the threshold voltage of the Vg-Ig property.

In the third exemplary embodiment, the ion sensitive insulating film is the thermal oxide film 26. Thus, the number of defects such as the pin holes in the ion sensitive insulating film to be the cause for immersion of the sensing solution is extremely small, so that the manufacturing yield can be increased. Other structures, operations, and effects of the third exemplary embodiment are the same as those of the first and second exemplary embodiments.

Example 5

Next, Example 5 which is a more concrete form of the third exemplary embodiment will be described by referring to FIGS. 6A and 6B.

As shown in FIG. 6A, an alloy material having molybdenum as the main component was deposited by sputtering on the silicon substrate 11 where the thermal oxide film 10 having a thickness of 100 nm was formed, and the source 13$s$ and the drain electrode 13$d$ were formed by using a photolithography process constituted with application of resist, exposure, development, etching, and exfoliation of the resist.

Subsequently, an oxide semiconductor film constituted with In—Ga—Zn—O was deposited to have a thickness of 50 nm by a sputtering method as the semiconductor active layer 12, and it was patterned to a desired island shape by a photolithography process. After the patterning, annealing processing was performed in the air at 400° C. for one hour.

Then, a silicon oxide film having a thickness of 300 nm was deposited at 350° C. by a plasma CVD method, and it was patterned to form the gate insulating film 20.

Further, a molybdenum metal was deposited by sputtering, and the molybdenum metal was etched by using a phosphoric-acid based solution after patterning the resist to form the gate electrode 19 in a desired shape.

As shown in FIG. 6B, resist is patterned on the back surface of the silicon substrate 11, and the part of the silicon substrate 11 located under the semiconductor active layer 12 was removed by etching to expose the thermal oxide film 26 located under the semiconductor active layer 12.

Thereafter, formed was a structure in which only the surface of the thermal oxide film 10 located under the semiconductor active layer 12 was exposed and the other part was covered by a protection film 15 that is constituted with an epoxy resin. In such structure, the exposed thermal oxide film 26 functions as the ion sensitive insulating film.

Since the ion sensitive insulating film (the thermal oxide film 26) and the gate insulating film 20 were both the silicon oxide films made with a same material, the film thickness of the ion sensitive insulating film (the thermal oxide film 26) was formed thinner than the film thickness of the gate insulating film (the plasma CVD film) 20 in order to make the electrostatic capacitance of the ion sensitive insulating film (the thermal oxide film 26) larger than the electrostatic capacitance of the gate insulating film 20. Such control of the capacitance values according to the difference between film thickness can be done also in Examples 1 to 3 described above.

The TFT having the above-described structures was dipped in a MacIlvaine buffer solution that is the sensing-target substance 16, and the reference electrode 17 constituted with platinum was placed in the MacIlvaine buffer solution.

0.5 V was applied to the drain electrode 13d of the TFT ion sensor 105 having the above-described structures, and the source electrode 13s and the reference electrode 17 were set to the ground potential (0 V). Further, the gate voltage was changed in a range of −2 V to +7 V in such biased state, and the Vg-Id property in the buffer solution of each pH was measured at a room temperature. As a result, the sensing sensitivity higher than 59 mV/pH as the theoretical limit that is determined from the Nernst formula was acquired. Further, the thermal oxide film 26 is extremely minute and has almost no pin-hole defects, so that high-yield manufacture can be achieved.

Fourth Exemplary Embodiment

Figure 7A:
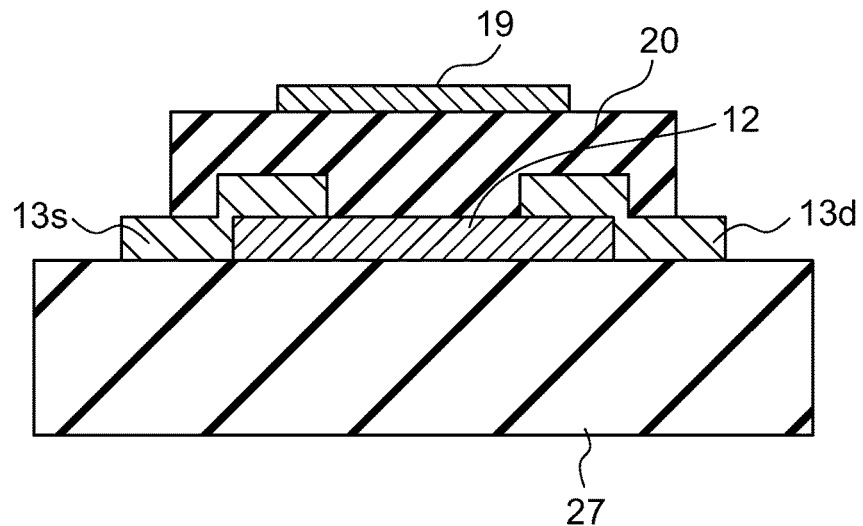
FIGS. 7A and 7B are sectional views showing a TFT ion sensor of a fourth exemplary embodiment and Example 6.
Figure 7B:
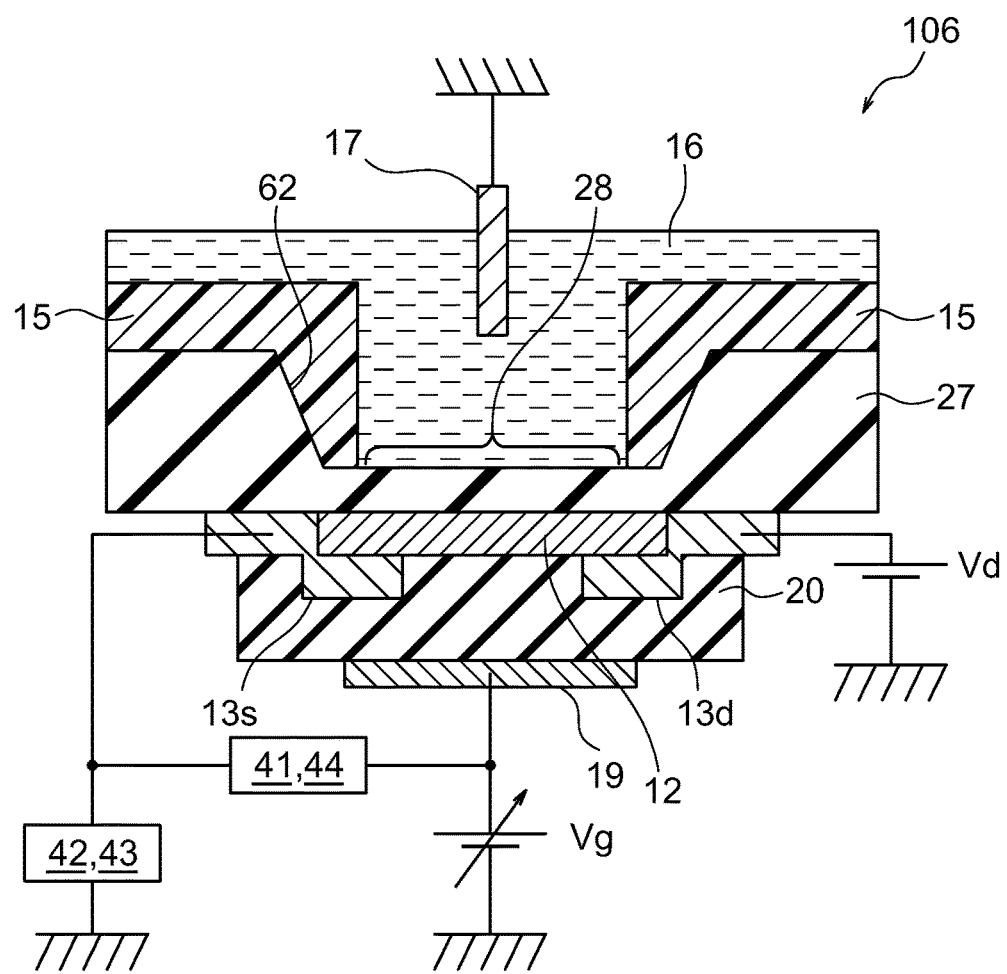

FIGS. 7A and 7B are sectional views showing a TFT ion sensor 106 according to a fourth exemplary embodiment.

As shown in FIG. 7A, a source electrode 13s, a drain electrode 13d, an island shaped semiconductor active layer 12, a gate insulating film 20, and a gate electrode 19 are formed in this order on an insulating substrate 27 that is formed with a material having a higher relative dielectric constant than that of the silicon oxide.

Further, as shown in FIG. 7B, a recessed part 62 is provided in the insulating substrate 27 on the opposite side from the semiconductor active layer 12 so that a thin part (an insulating substrate 28) of the insulating substrate 27 is exposed. That is, the remaining insulating substrate 28 located under the semiconductor active layer 12 is exposed through removing the part of the insulating substrate 27 which is located under the island shaped semiconductor active layer 12. The exposed insulating substrate 28 functions as the ion sensitive insulating film. Further, the insulating substrate 28 part out of the insulating substrate 27 is exposed, and the part other than the insulating substrate 28 is covered by a protection insulating film 15. The TFT having such structures is placed in a sensing-target substance 16, and a reference electrode 17 is provided in the sensing-target substance 16.

The electrostatic capacitance per unit area of the ion sensitive insulating film (the insulating substrate 28) is set to be larger than the electrostatic capacitance per unit area of the gate insulating film 20 in the TFT ion sensor 106 having the above-described structures, and the change in the ion concentration in the sensing-target substance 16 is detected from the change in the threshold voltage of the Vg-Id property.

In the fourth exemplary embodiment, the insulating substrate 27 constituted with monocrystalline is used and utilized as the ion sensitive insulating film. Thus, the number of defects such as the pin holes in the ion sensitive insulating film to be the cause for immersion of the sensing solution is extremely small, so that the manufacturing yield can be increased.

Example 6

Next, Example 6 which is a more concrete form of the fourth exemplary embodiment will be described by referring to FIGS. 7A and 7B.

As shown in FIG. 7A, an oxide semiconductor film constituted with In—Ga—Zn—O was deposited to have a thickness of 50 nm as the semiconductor active layer 12 on the insulating substrate 27 that is a monocrystalline substrate in a thickness of 0.3 mm constituted with strontium titanate, and it was patterned to a desired island shape by a photolithography process.

Subsequently, a titanium metal was deposited by sputtering, and the source electrode 13s and the drain electrode 13d were formed by using a photolithography process constituted with application of resist, exposure, development, etching, and exfoliation of the resist. After forming the source electrode 13s and the drain electrode 13d, annealing processing was performed in the air at 400° C. for one hour.

Subsequently, a silicon oxide film having a thickness of 300 nm was deposited as the gate insulating film 20 at a substrate temperature of 350° C. by using a plasma CVD method.

Further, a molybdenum metal was deposited by sputtering, and the molybdenum metal was etched by using a phosphoric-acid based solution after patterning the resist to form the gate electrode 19 in a desired shape.

As shown in FIG. 7B, resist was patterned on the back surface of the insulating substrate 27 constituted with strontium titanate monocrystalline and a part of the insulating substrate 27 located under the island shaped semiconductor active layer 12 was removed by etching to leave the insulating substrate 28 in a thickness of 1 μm.

Thereafter, formed was a structure in which only the surface of the remained insulating substrate 28 was exposed and the other part was covered by a protection film 15 that is constituted with an epoxy resin. In such structure, the exposed insulating substrate 28 functions as the ion sensitive insulating film. Note here that the relative dielectric constant of the monocrystalline strontium titanate is 300 that is extremely large, so that the electrostatic capacitance of the ion sensitive insulating film (the insulating substrate 28) constituted with the strontium titanate becomes extremely larger than the electrostatic capacitance of the gate insulating film 20 even when the thickness is 1 μm as described above.

The TFT having the above-described structures was dipped in a MacIlvaine buffer solution that is the sensing-target substance 16, and the reference electrode 17 constituted with platinum was placed in the MacIlvaine buffer solution.

0.5 V was applied to the drain electrode 13d of the TFT ion sensor 105 having the above-described structures, and the source electrode 13s and the reference electrode 17 were set to the ground potential (0 V). Further, the gate voltage was changed in a range of −2 V to +7 V in such biased state, and the Vg-Id property in the buffer solution of each pH was measured at a room temperature. As a result, the sensing sensitivity considerably higher than 59 mV/pH as the theoretical limit that is determined from the Nernst formula was acquired.

Such high sensitivity is resulted from the extremely high relative dielectric constant of the strontium titanate. Further, the monocrystalline strontium titanate is extremely minute and has almost no pin-hole defects, so that high-yield manufacture can be achieved. Other structures, operations, and effects of the fourth exemplary embodiment are the same as those of the first to third exemplary embodiments.

Fifth Exemplary Embodiment

Figure 8:
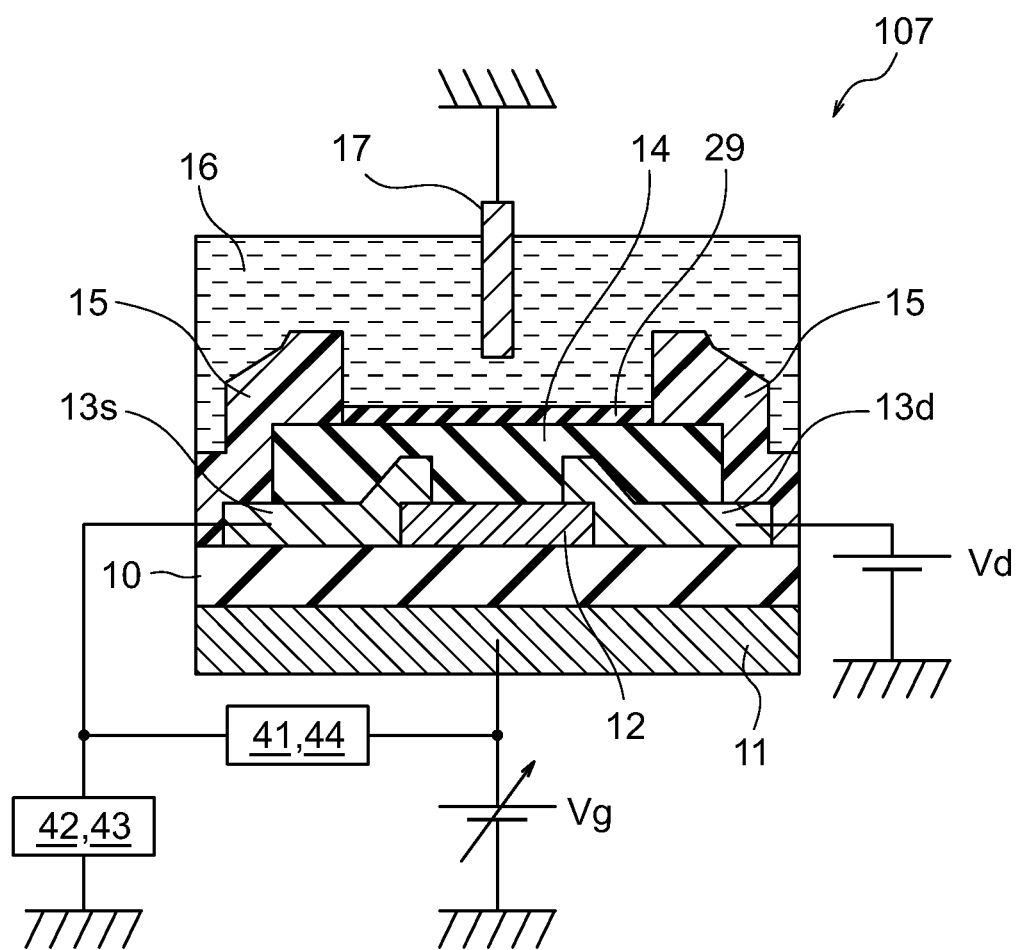
FIG. 8 is a sectional view showing a TFT ion sensor of a fifth exemplary embodiment.

FIG. 8 is a sectional view showing a TFT ion sensor 107 according to a fifth exemplary embodiment.

In the fifth exemplary embodiment, described is a TFT ion sensor 107 which has a reverse-stagger type oxide semiconductor TFT as a basic structure and the sensitivity for a specific ion is given. In the TFT ion sensor 107, an ion selective sensing film 29 is formed on a top layer of an ion sensitive insulating film 14 to give the sensitivity for a specific ion. The ion selective sensing film 29 can be broadly classified into a positive ion selective sensing film and a negative ion selective sensing film.

As the positive ion selective sensing film, it is possible to employ a thin film acquired by solidifying, with a resin material, a compound having polypeptide or crown ether of valinomycin or the like to be a ligand as the basic skeleton. However, it is not limited only to those. The ligand is a substance which specifically binds to a specific receptor.

The method for fabricating the positive ion selective sensing film will be described. First, a ligand and a resin material to be the base material of the positive ion selective sensing film are dissolved in a proper organic solvent. As the base material, polyvinyl chloride can be used, for example. As the organic solvent, tetrahydrofuran can be used, for example. Note, however, that the material and the solvent are not limited only to those.

The organic solvent in which the ligand and the base material are dissolved is dropped on the top layer of the ion sensitive insulating film 14, and the organic solvent is volatilized and dried while applying heat as appropriate. Through this operation, a thin film formed by solidifying the ligand can be acquired. It is preferable to control the film thickness within a range of 10 nm to 1000 nm.

Through using such positive ion selective sensing film as the ion selective sensing film 29, it is possible to provide the TFT ion sensor 107 to which the specific sensitivity for Na ions, K ions, and Ca ions is given.

As the negative ion selective sensing film, an insoluble metallic salt thin film can be used. As the metallic salt thin film, $LaF_3$, $AgCl$, $AgBr$, $AgI$, $Ag_2S$, or insoluble metallic salt similar to those can be used. However, it is not limited only to those. For forming the negative ion selective sensing film, a method which compression-molds powders into a thin film or a method which dissolves powders into a proper solvent and performs spin application can be used. It is preferable to control the film thickness to fall within a range of 10 nm to 1000 nm.

Through using such negative ion selective sensing film as the ion selective sensing film 29, it is possible to provide the TFT ion sensor 107 to which the specific sensitivity for Ag ions, Cl ions, Br ions, and S ions is given. Other structures, operations, and effects of the fifth exemplary embodiment are the same as those of the first to fourth exemplary embodiment.

Sixth Exemplary Embodiment

Figure 9:
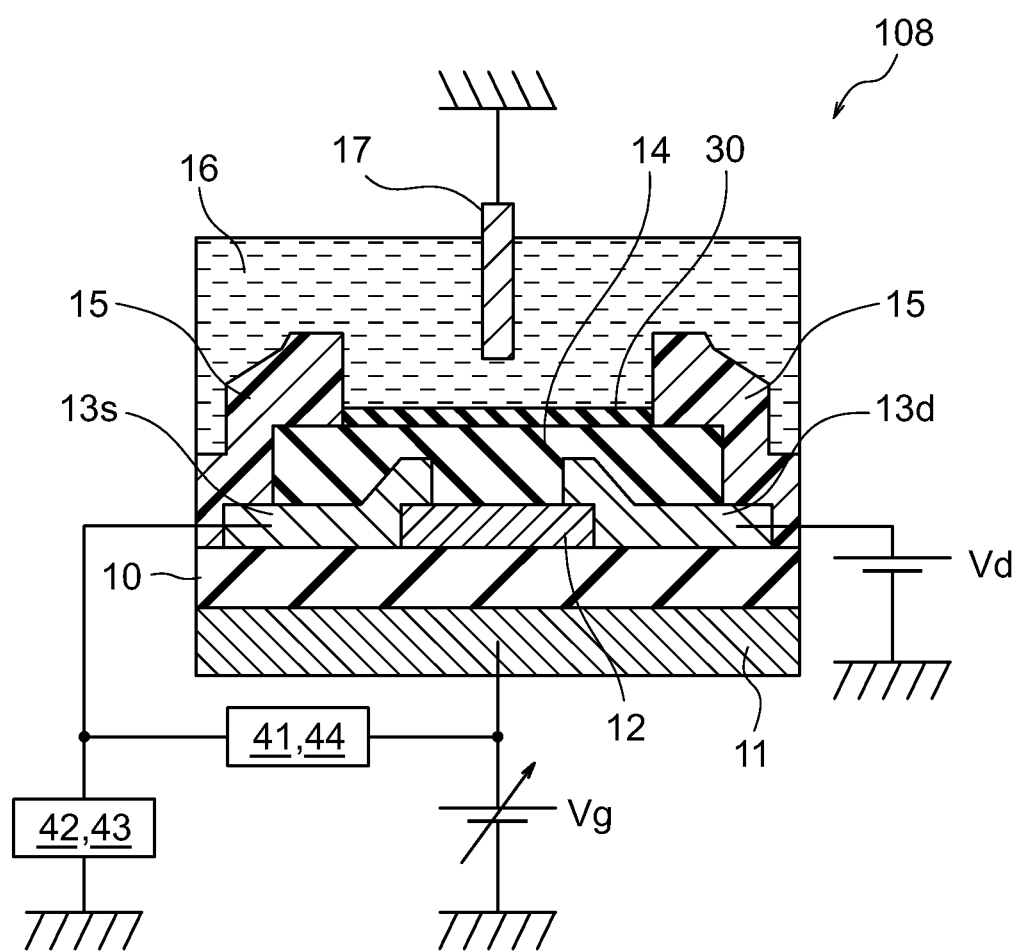
FIG. 9 is a sectional view showing a TFT ion sensor of a sixth exemplary embodiment.

FIG. 9 is a sectional view showing a TFT ion sensor 108 according to a sixth exemplary embodiment.

In the sixth exemplary embodiment, described is a TFT ion sensor 108 which has a reverse-stagger type oxide semiconductor TFT as a basic structure and the sensitivity for a substance to be a substrate of an enzyme 30 is given through solidifying the enzyme 30 to an ion sensitive insulating film 14.

The TFT ion sensor 108 is provided with the sensitivity for a specific bio-substance by forming the enzyme 30 having the substrate specificity for the specific bio-substance on the top layer of the ion sensitive insulating film 14, thereby having a bio-sensing function. As an example, the enzyme 30 is solidified on the ion sensitive insulating film 14, and an enzyme reaction with the substrate is promoted in the vicinity of the ion sensitive insulating film 14. Thereby, the TFT ion sensor 108 detects the substrate concentration through changing the hydrogen ion concentration in the vicinity of the ion sensitive insulating film 14 and detecting the change in the hydrogen ion concentration.

The enzyme 30 is for giving an affinity for the specific bio-substance to be the substrate, and it has a function of changing the hydrogen ion concentration, i.e., pH, in the vicinity of the ion sensitive insulating film 14 by generating the hydrogen ions as by-products by reacting with the substrate in the vicinity of the ion sensitive insulating film 14. As shown in the first exemplary embodiment, it is possible to give the sensitivity for the hydrogen ion by using the insulating oxide film as the ion sensitive insulating film 14. According to the sixth exemplary embodiment, the concentration can be measured indirectly through quantitating the hydrogen ions generated by the enzyme reaction.

As the enzyme 30 solidified to the ion sensitive insulating film 14, it is possible to use dehydrogenases such as glucose dehydrogenase, alcohol dehydrogenase, aldehyde dehydrogenase, glycerol dehydrogenase, glutamate dehydrogenase, pyruvate dehydrogenase, malate dehydrogenase, lactate dehydrogenase, and the like. Through selecting the proper enzyme, it becomes possible to correspond to various kinds of measurement targets.

For solidifying the enzyme 30, a self-assembled monolayer film (referred to as "SAM (Self-Assembled Monolayer)" film hereinafter) can be used. The SAM film links by having the hydroxyl group of the ion sensitive insulating film 14 as the start point and functions as a linker between with the enzyme 30. As the method for depositing the SAM film, used may be spin coating, dip coating, and vacuum deposition. However, the methods are not limited only to those. As the materials for the SAM film, it is possible to use those which modify the metal surface via a thiol group and to use a silane coupling agent. However, the materials are not limited only to those as long as a proper linkage strength can be acquired.

In a case where glucose is used as the substrate and glucose dehydrogenase is used as the enzyme 30 as an example of the sixth exemplary embodiment, a following reaction is promoted in the vicinity of the ion sensitive insulating film 14 to which the enzyme 30 is solidified.

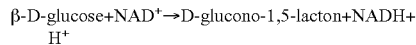

$\beta$-D-glucose+NAD$^+$→D-glucono-1,5-lacton+NADH+ H$^+$

That is, nicotinamide adenine dinucleotide (NAD) function as a coenzyme, $\beta$-D-glucose is oxidized, and D-glucono-1,5-lacton and the hydrogen ions are generated. At this time, the generated hydrogen ions are in an equivalent amount with the amount of $\beta$-D-glucose, so that the degree of $\beta$-D-glucose of a test sample can be measured by detecting the change in the hydrogen ions. Other structures, operations, and effects of the sixth exemplary embodiment are the same as those of the first to fifth exemplary embodiments.

Seventh Exemplary Embodiment

Figure 10:
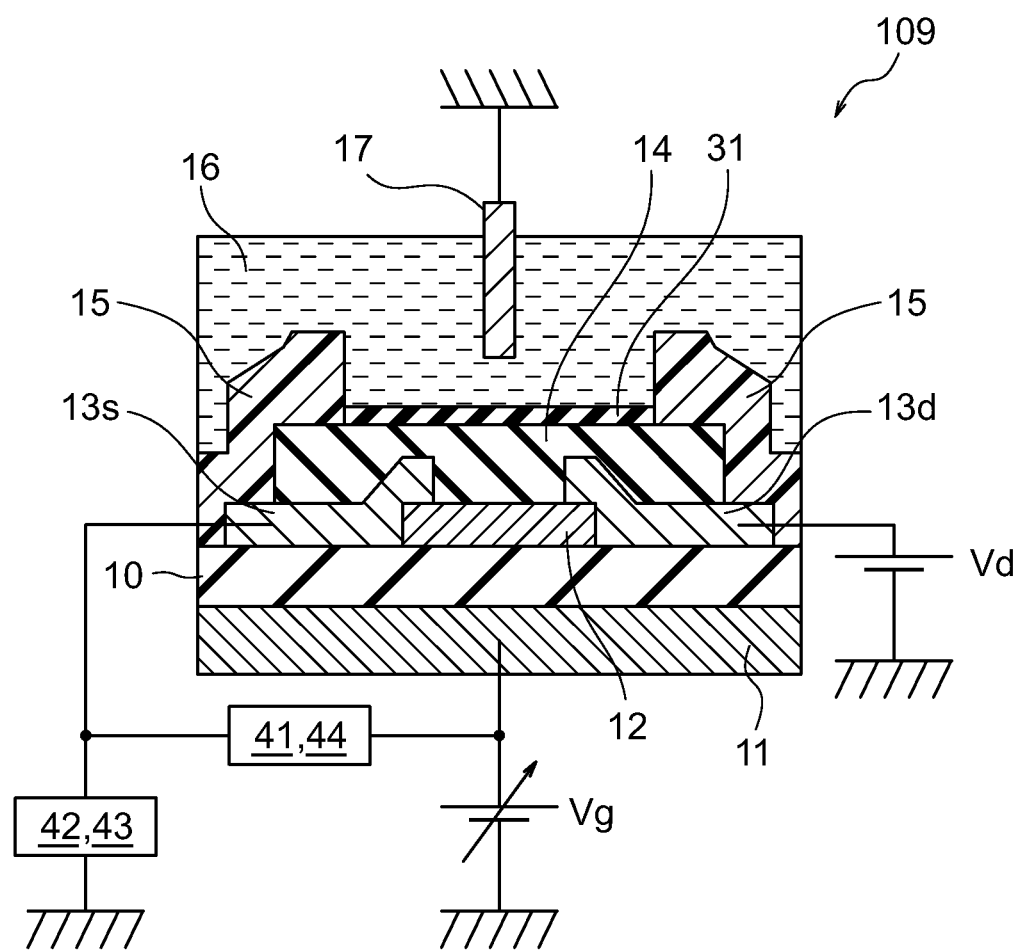
FIG. 10 is a sectional view showing a TFT ion sensor of a seventh exemplary embodiment.

FIG. 10 is a sectional view showing a TFT ion sensor 109 according to a seventh exemplary embodiment.

In the seventh exemplary embodiment, described is the TFT ion sensor 109 which has a reverse-stagger type oxide semiconductor TFT as a basic structure and the sensitivity for a specific substance is given through solidifying a bio-substance to an ion sensitive insulating film 14. The TFT ion sensor 109 is provided with a ligand 31 exhibiting an affinity for the specific bio-substance formed on the top layer of the ion sensitive insulating film 14. Therefore, it has the sensitivity for the specific bio-substance and includes a bio-sensing function.

The ligand 31 is for giving an affinity for the specific bio-substance, and it generates a change in the interface potential of the ion sensitive insulating film 14 by being linked to the bi-substance exhibiting the affinity in the vicinity of the ion sensitive insulating film 14. Through detecting the change in the interface potential by the reverse-trigger type oxide semiconductor TFT formed underneath, the amount of the bio-substance linked to the ligand 31 can be grasped. That is, it becomes possible to measure the concentration of the target substance contained in the test sample.

As the ligand 31, sugar, protein, DNA (DeoxyriboNucleic Acid), RNA (RiboNucleic Acid) or the like can be used. For example, as sugar, it is possible to use a monosaccharide such as glucose, galactose, fructose, ribose, or the like, and oligosaccharide as well as a polysaccharide in which those are combined. As the protein, enzyme, antibody, bio-active peptide, or the like can be used. However, the protein to be used is not limited only to those. Further, a sugar-protein complex, a sugar-lipid complex, and the like exhibiting biological activity can be used as well in a same manner. When DNA or RNA is used as the ligand 31, the ion sensor can also be used as a means for detecting DNA or RNA having complementary configurations.

When a sugar chain exhibiting biological activity is used as the ligand 31 as an example of the seventh exemplary embodiment, the ion sensor can be used as a means for detecting lectin exhibiting the affinity for the sugar chain. Inversely, when lectin is used as the ligand 31, it can be applied to evaluation of the substrate specificity of lectin through comprehensively evaluating the affinity for various kinds of sugar chains.

When an antibody is used as the ligand 31 as an example of the seventh exemplary embodiment, the ion sensor can be used as a means for detecting protein to be an antigen. Inversely, when an antigen is used as the ligand, it can be employed also as a means for searching an effective antibody.

In a case where giant molecules of protein or the like are used as the ligand 31, it is effective to set the region where linkage of the ligand 31 and the target substance is promoted for improving the detection sensitivity to fall within a Debye length. For example, when an antibody is used as the ligand 31, it is effective to use a variant in which the molecule having only the linked part with the antibody is decreased in size. Other structures, operations, and effects of the seventh exemplary embodiment are the same as those of the first to sixth exemplary embodiment.

Eighth Exemplary Embodiment

In order to detect the electric double layer potential difference generated on the surface of the ion sensitive insulating film via the change in the Vg-Id property, it is effective to decrease the defects on the surface of the semiconductor active layer to be in contact with the ion sensitive insulating film, i.e., the defects of the top channel. As the property of the TFT ion sensor, it is ideal to be able to acquire a parallel shift of the Vg-Id property corresponding to the electric double layer potential. However, when there are highly dense defects existing in the top channel, it is not possible to acquire an ideal parallel shift and the correlation between the electric double layer potential and the Vg-Id property shift amount may break down in some cases. In order to suppress the defects in the top channel, it is important to suppress exposure to drugs and plasma in the fabricating steps as much as possible. For example, it is effective to use a stencil mask.

By using a dual gate structure TFT having different defect density of the top channel, the difference in the sensitivity for the top gate applied voltage will be described. Note here that the dual gate structure is a structure which has a second gate electrode (a top gate electrode) on the ion sensitive insulating film 14 in addition to the gate electrode constituted with the silicon substrate 11, when referring to FIG. 1. To apply the top gate voltage in the dual gate structure TFT is an action equivalent to generation of the electric double layer potential on the surface of the ion sensitive insulating film 14 in the TFT ion sensor.

For example, through forming the interface (the top channel) between the island shaped semiconductor active layer 12 and the ion sensitive insulating film 14 without exposing to plasma, medical fluids, and the like, the defect density can be decreased. In order to achieve it, there is a method which deposits and forms the island shaped semiconductor active layer 12, the source electrode 13s, and the drain electrode 13d into desired shapes by using a stencil mask or a metal mask, for example. Such method can be employed for the cases of the TFT ion sensors shown in FIG. 3 to FIG. 5. Through decreasing the defect density of the top channel in this manner, it is possible to manufacture the highly sensitive TFT ion sensors with high yield.

In the meantime, when the surface of the island shaped semiconductor active layer is contaminated with a medical fluid or damaged by plasma while being processed, the defect density is increased. For example, when performing etching processing on the source electrode 13s and the drain electrode 13d in the structure shown in FIG. 1, defects may be formed on the surface of the island shaped semiconductor active layer 12 by an acid solvent or plasma in some cases.

The result of evaluation on the sensitivity for the top gate voltage of the dual gate structure TFT with different defect density will be described. In the dual gate structure TFT with low defect density of the top channel, a parallel shift of the Vg-Id property is observed for application of both the positive and negative top gate voltages. In the meantime, in the dual gate structure TFT with high defect density of the top channel, a parallel shift of the Vg-Id property is observed for application of the negative top gate voltage while decrease in the threshold property is observed for application of the positive top gate voltage so that there is no parallel shift in the Vg-Id property. Even in the case where a parallel shift of the Vg-Id property is not observed, the effect of the present invention for achieving the high sensitivity can be acquired without a question. In order to evaluate the applied top gate voltage from the shift of the Vg-Id property, it is more preferable to use the dual gate structure TFT with low defect density with which a parallel shift of the Vg-Id property can be acquired by applying the positive and negative voltages. The tendency of achieving the top gate effect is reflected upon the TFT ion sensors shown in each of the exemplary embodiments which use the TFT as the basic structure. Therefore, needless to say, to decrease the defect density of the top channel is more effective for increasing the sensitivity of the TFT ion sensor according to the present invention.

As a quantitative index of the top channel defects, there is a state of linkage on the surface of the oxide semiconductor in a case of using an oxide semiconductor as the island shaped semiconductor active layer, for example. In a case of employing dry etching using fluorine-based gas such as $SF_6$, $CF_4$, or the like for patterning the source-drain electrodes on the oxide semiconductor, linkages with fluorine are generated on the surface of the oxide semiconductor. This phenomenon can be evaluated quantitatively by XPS (X-ray Photoelectron Spectroscopy), and it can be observed as a shift of the peak showing linkages of In3d5, Ga2p3, and Zn2p3 to the high energy side. When the surface of the oxide semiconductor is exposed to Ar plasma or the like for a long time, linkages of In—O, Ga—O, and Zn—O are cleaved, and oxygen depletion is generated on the surface of the oxide semiconductor. This phenomenon can be evaluated quantitatively by XPS, and it can be observed as a shift of the peak showing linkages of In3d5, Ga2p3, and Zn2p3 to the low energy side. It is possible to estimate the defect density from the shifted peak intensity. The defect density of $1$-$10^{21}$ cm$^{-3}$ or less is desirable.

As described above, through suppressing defects on the top channel which can be evaluated quantitatively by XPS, it becomes possible to achieve the TFT ion sensor with still higher sensitivity exhibiting high responsiveness to the electric double layer potential.

Ninth Exemplary Embodiment

Figure 11:
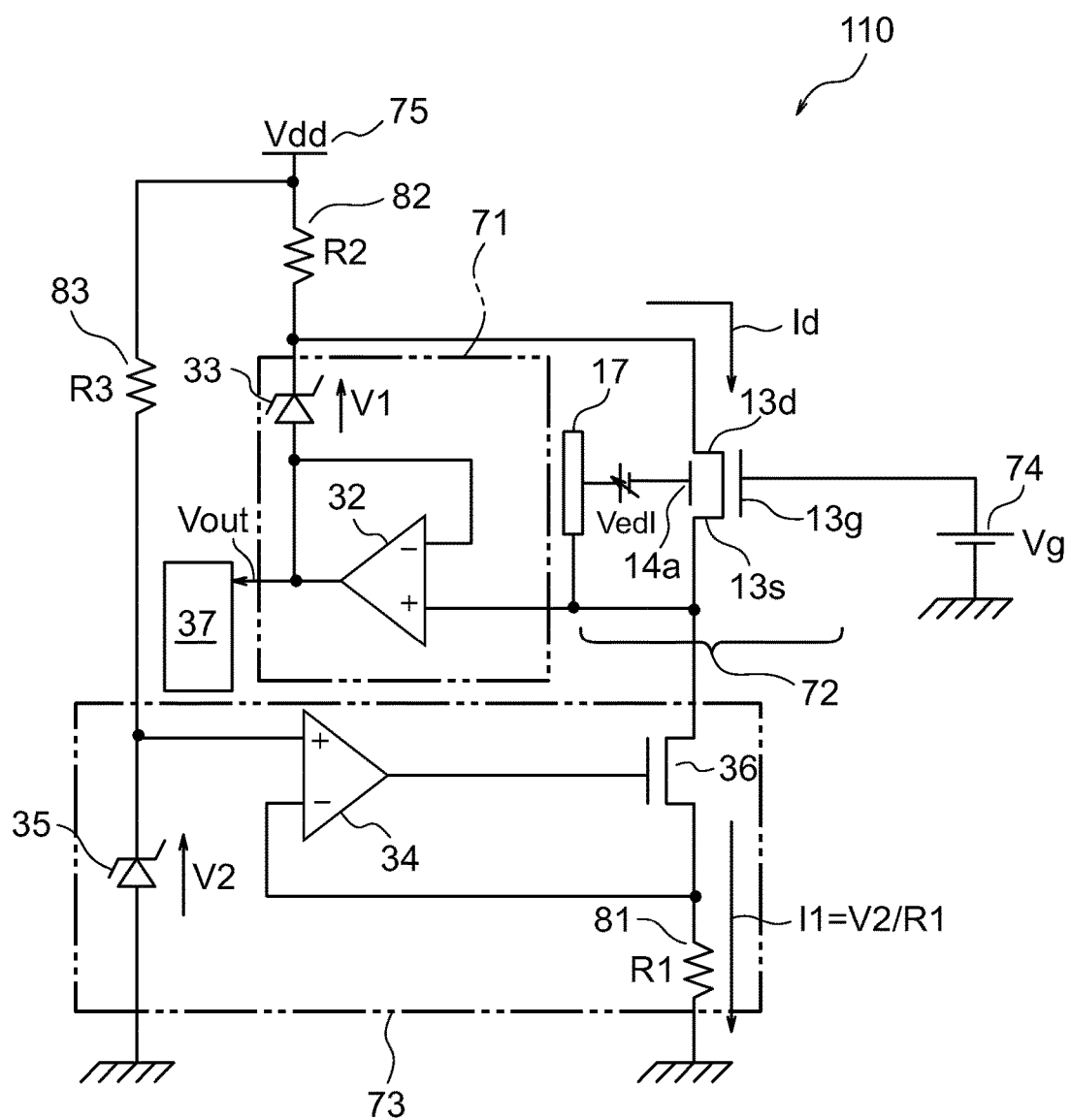
FIG. 11 is a circuit diagram showing a TFT ion sensor apparatus of a ninth exemplary embodiment and Example 7.

FIG. 11 is a circuit diagram showing a TFT ion sensor apparatus 110 according to a ninth exemplary embodiment. In the ninth exemplary embodiment, a prescribed potential for the source potential is supplied to a reference electrode 17 (a same potential as that of the source potential is supplied to the reference electrode 17 in FIG. 11), a potential difference between a gate electrode 13g and a source electrode 13s is controlled so that a prescribed current flows between the source electrode 13s and a drain electrode 13d (the potential of the gate electrode 13g is fixed, and the potential of the source electrode 13s fluctuates in FIG. 11), and the potential difference between the gate electrode 13g and the source electrode 13s resulted from the ion concentration in a sensing-target substance is read out to detect the ion concentration in the sensing-target substance.

A TFT ion sensor 72 corresponds to a structure acquired by eliminating a voltage detection unit, a current detection unit, a voltage control unit, and a current control unit from the TFT ion sensors described in the first to eighth exemplary embodiments. The structure acquired by eliminating the TFT ion sensor 72 from the TFT ion sensor apparatus 110 corresponds to an example of the "detection circuit" in the scope of the appended claims. A potentiometer 37 and a constant current circuit 73 correspond to examples of the voltage detection unit 41 and the voltage control unit 43 shown in FIG. 1 and the like, respectively.

Example 7

Example 7 which is a more concrete form of the ninth exemplary embodiment will be described by referring to FIG. 11.

A constant voltage circuit 71 includes a first operation amplifier 32 and a first Zener diode 33 as a constant voltage source, and fixes the potential difference between the source electrode 13s and the drain electrode 13d of the TFT ion sensor 72. Herein, the potential difference between the source electrode 13s and the drain electrode 13d is fixed to an inverse yield voltage V1 of the first Zener diode 33.

A constant current circuit 73 is connected to the source electrode 13s, and fixes the current flown between the source electrode 13s and the drain electrode 13d of the TFT ion sensor 72. The main structural elements of the constant current circuit 73 are a second operation amplifier 34, a second Zener diode 35, a transistor 36, and a first resistor 81. Herein, the current value flown between the source electrode 13s and the drain electrode 13d is fixed to a current value I1 that is the value acquired by dividing an inverse yield voltage V2 of the second Zener diode 35 by a resistance value R1 of the first resistor 81.

The specific circuit structure is described as follows. The gate electrode 13g of the TFT ion sensor 72 is connected to one of the nodes of a direct current voltage source 74 (gate voltage Vg), and the other node of the direct current voltage source 74 is connected to the ground. The source electrode 13s of the TFT ion sensor 72 is connected to the reference electrode 17. The drain electrode 13d of the TFT ion sensor 72 is connected to a direct current voltage source 75 (supply voltage Vdd) via a second resistor 82 (resistance value R2). The source electrode 13s of the TFT ion sensor 72 is connected to a noninverting input node of the first operation amplifier 32, and an inverting input node of the first operation amplifier 32 is connected to an output node of the first operation amplifier 32. Thereby, the first operation amplifier 32 operates as a voltage follower circuit. The output node of the first operation amplifier 32 is used as an output terminal of the TFT ion sensor apparatus 110. The potentiometer 37 is connected for reading out the output voltage Vout. The inverting input node of the first operation amplifier 32 is connected to the anode of the first Zener diode 33, and the cathode of the first Zener diode 33 is connected to the drain electrode 13d of the TFT ion sensor 72.

The source electrode 13s of the TFT ion sensor 72 is connected to the drain node of the transistor 36, and the source node of the transistor 36 is connected to the ground via the first resistor 81 (resistance value R1). The gate electrode of the transistor 36 is connected to the output node of the second operation amplifier 34, and the inverting input node of the second operation amplifier 34 is connected to the source node of the transistor 36. The noninverting input node of the second operation amplifier is connected to the cathode node of the second Zener diode 35, the anode node of the second Zener diode 35 is connected to the ground, and the cathode node of the second Zener diode 35 is connected to the direct current voltage source 75 via a third resistor 83 (resistance value R3).

Figure 12:
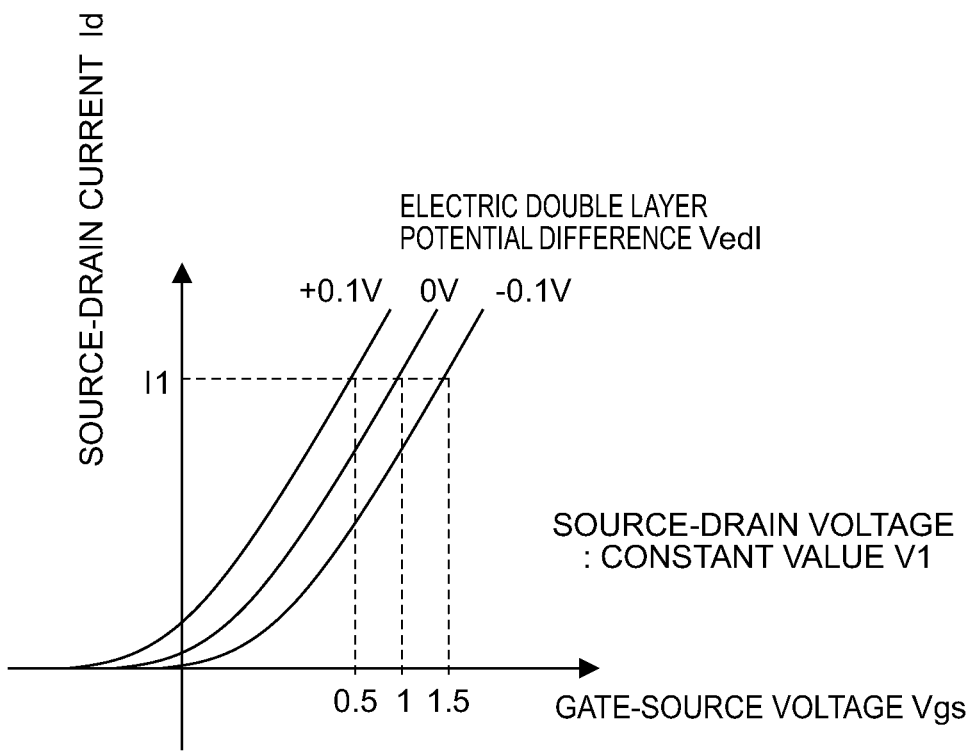
FIG. 12 is a graph showing the measurement principle of the TFT ion sensor apparatus of Example 9.

A measurement method executed by using the TFT ion sensor apparatus 110 by having the potential of the source electrode 13s of the TFT ion sensor 72 as the reference will be described. The lateral axis of FIG. 12 shows the gate-source voltage Vgs that is the potential of the gate electrode 13g by having the potential of the source electrode 13s as the reference. Further, the longitudinal axis shows the source-drain current Id flown between the source electrode 13s and the drain electrode 13d. That is, schematically shown herein is the Vgs-Id property.

Note here that the potential difference between the source electrode 13s and the drain electrode 13d is fixed to V1 as described above. When the ion concentration in a sensing-target substance changes and the electric double layer potential difference Vedl on the interface between the sensing-target substance and the ion sensitive insulating film 14, i.e., on an ion sensitive insulating film surface 14a, changes as +0.1 V, 0 V, −0.1 V, the gate-source voltage Vgs changes as 1.5 V, 1 V, 0.5 V for flowing the current value I1 that is fixed by the constant current circuit 73. The output voltage Vout of the TFT ion sensor apparatus 110 is equivalent to the source voltage Vs. Further, the gate-source voltage Vgs is equivalent to the difference between the gate voltage Vg and the source voltage Vs. Thus, the output voltage Vout becomes equivalent to the difference between the gate voltage Vg and the gate-source voltage Vgs.

Therefore, to read out how the output voltage Vout changes for flowing the constant current I1 by the potentiometer 37 in various kinds of ion concentrations is equivalent to reading out how the gate-source voltage Vgs changes for flowing the constant current I1. This is no other than detecting the shift amount of the Vg-Id property in various kinds of ion concentrations (as shown in FIG. 2).

In Example 7, the voltage between the source electrode 13s and the drain electrode 13d is fixed. Thus, there is also achieved such an effect that the output property of the TFT can be measured with high precision both in a saturated region and a linear region.

When performing the measurement by using the property of the saturated region of the TFT, the circuit shown in FIG. 11 can be simplified further. For example, the first Zener diode 33 shown in FIG. 11 can be omitted, and the constant voltage source 75 can be connected to the drain electrode 13d via the second resistor 82. Alternatively, the first Zener diode 33 and the second resistor 82 shown in FIG. 11 may be omitted, and the constant voltage source 75 may be connected directly to the drain electrode 13d.

As described above, through using the TFT ion sensors described in the first to eighth exemplary embodiments for the TFT ion sensor 72 of the ninth exemplary embodiment shown in FIG. 11, it is possible to achieve the TFT ion sensor apparatus 110 exhibiting the higher sensitivity than that of the related techniques.

Next, described is a phenomenon where the electric double layer potential difference is amplified through the mutual actions and the capacitance difference between the bottom-gate electric field and the top-gate electric field of the TFT ion sensor according to the ninth exemplary embodiment.

Each of source-drain currents Id, Id1, Id2 are approximated by following expressions provided that the source-drain current is Id, the source-drain current originated from the bottom-gate electric field is Id1, the source-drain current originated from the top-gate electric field is Id2, the drain voltage is Vd, the gate-source voltage is Vgs, the carrier-induced threshold voltage is Vt, the electric double layer potential difference is Vedl, the electrostatic capacitance per unit area of the gate insulating film is C, the electrostatic capacitance per unit area of the ion sensitive insulating film is nC (where n>1), the mobility of the carriers is μ, the channel width is W, and the channel length is L.

$$Id = Id1 + Id2 \quad (1)$$

$$Id1 = (W\mu C/L)\{(Vgs-Vt)Vd - Vd^2/2\} \quad (2)$$

$$Id2 = n(W\mu C/L)\{(Vedl-Vt)Vd - Vd^2/2\} \quad (3)$$

When Expressions (2) and (3) are substituted into Expression (1) and organized, following expressions can be acquired.

$$Id = (W\mu C/L)\{(Vgs-Vt)Vd - Vd^2/2\} + n(W\mu C/L)\{(Vedl-Vt)Vd - Vd^2/2\} \therefore Id/(W\mu C/L) = Vd(Vgs+nVedl) - Vt \cdot Vd(n+1) - Vd^2(n+1)/2 \therefore Vgs + nVedl = Id/(VdW\mu C/L) + Vt(n+1) + Vd(n+1)/2 \quad (4)$$

In the ninth exemplary embodiment, the right side of Expression 4 is a constant, so that a following expression applies.

$$Vgs + nVedl = \text{constant} \quad (5)$$

When the electric double layer potential difference Vedl changes by "ΔV", the gate-source voltage Vgs changes by n-times "−ΔV" as it is evident from Expression (5) described above.

In the example shown in FIG. 12, Vgs=1 when Vedl=0. Thus, the right side of Expression (5) is always "1". In this case, assuming that n=5 in Expression 5, Vgs=0.5 when Vedl=0.1, and Vgs=1.5 when Vedl=−0.1 as shown in FIG. 12.

Further, in a case where the gate-source voltage Vgs is fixed and the source-drain current Id is variable, a following expression can be acquired.

$$Id = Id1 + Id2 \quad (6)$$

$$= Id1(\text{constant}) + n(W\mu C/L)\{(Vedl - Vt)Vd - Vd^2/2\}$$

As evident from Expression (6), through setting the electrostatic capacitance of the ion sensitive insulating film to be n-times the electrostatic capacitance of the gate insulating film, the change in the source-drain current Id (i.e., the sensitivity) for the change in the electric double layer potential difference Vedl can be increased by n-times compared to the case where the electrostatic capacitance of the ion sensitive insulating film is set to be equivalent to the electrostatic capacitance of the gate insulating film.

While the present invention has been described above by referring to each of the exemplary embodiments, the present invention is not limited only to each of the exemplary embodiments described above. Various changes and modifications which can occur to those skilled in the art can be applied to the structures and details of the present invention. Further, the present invention includes the structures acquired by mutually and properly combining a part of or a whole part of the structures of each of the above-described exemplary embodiments.

While a part of or a whole part of the exemplary embodiments can be summarized as following Supplementary Notes, the present invention is not limited only to the following structures.

(Supplementary Note 1)

A TFT ion sensor which includes:

a semiconductor active layer to which a source electrode and a drain electrode are connected;

a gate insulating film and a gate electrode provided on one of surfaces of the semiconductor active layer;

an ion sensitive insulating film provided on the other surface of the semiconductor active layer; and a reference electrode provided at a position spatially isolated from the ion sensitive insulating film, wherein:

an electrostatic capacitance per unit area of the ion sensitive insulating film is larger than an electrostatic capacitance per unit area of the gate insulating film; and a voltage detection unit for reading out a potential difference between the source electrode and the gate electrode is provided further.

(Supplementary Note 2)

A TFT ion sensor which includes:

a semiconductor active layer to which a source electrode and a drain electrode are connected;

a gate insulating film and a gate electrode provided on one of surfaces of the semiconductor active layer;

an ion sensitive insulating film provided on the other surface of the semiconductor active layer; and a reference electrode provided at a position spatially isolated from the ion sensitive insulating film, wherein:

an electrostatic capacitance per unit area of the ion sensitive insulating film is larger than an electrostatic capacitance per unit area of the gate insulating film; and a current detection unit for reading out a current flown in the source electrode or the drain electrode is provided further.

(Supplementary Note 3)

The TFT ion sensor as depicted in Supplementary Note 1, wherein the potential difference between the source electrode and the gate electrode is a potential difference acquired by multiplying a value of a ratio that is acquired by dividing the electrostatic capacitance per unit area of the ion sensitive insulating film by the electrostatic capacitance per unit area of the gate insulating film to a potential difference generated between the ion sensitive insulating film and a sensing-target substance that is disposed on the ion sensitive insulating film.

(Supplementary Note 4)

The TFT ion sensor as depicted in Supplementary Note 1 or 3, which further includes a voltage control unit which controls the potential difference between the source electrode and the gate electrode so that a constant current flows between the source electrode and the drain electrode.

(Supplementary Note 5)

The TFT ion sensor as depicted in Supplementary Note 2, which further includes a current control unit which controls the current flown between the source electrode and the drain electrode so that the potential difference between the gate electrode and the source electrode becomes constant.

(Supplementary Note 6)

The TFT ion sensor as depicted in any one of Supplementary Notes 1 to 5, wherein the gate electrode, the gate insulating film, the semiconductor active layer, the source electrode as well as the drain electrode, and the ion sensitive insulating film are provided in this order on a substrate.

(Supplementary Note 7)

The TFT ion sensor as depicted in any one of Supplementary Notes 1 to 5, wherein:

a thermal oxide film, the source electrode as well as the drain electrode, the semiconductor active layer, the gate insulating film, and the gate electrode are provided in this order on a silicon substrate; and an opening part is provided in the silicon substrate so that the thermal oxide film located under the semiconductor active layer is exposed.

(Supplementary Note 8)

The TFT ion sensor as depicted in any one of Supplementary Notes 1 to 5, wherein:

the semiconductor active layer, the source electrode as well as the drain electrode, the gate insulating film, and the gate electrode are provided in this order on an insulating substrate; and a recessed part is provided on the insulating substrate on an opposite side from the semiconductor active layer so that a thin part of the insulating substrate is exposed.

(Supplementary Note 9)

The TFT ion sensor as depicted in any one of Supplementary Notes 1 to 8, wherein the ion sensitive insulating film is a monolayer film formed with one selected from tantalum oxide, hafnium oxide, aluminum oxide, barium titanate, strontium titanate, and a silicon nitride, or a laminated film formed with two or more of those.

(Supplementary Note 10)

The TFT ion sensor as depicted in any one of Supplementary Notes 1 to 9, wherein an ion selective sensitive film exhibiting sensitivity for a specific ion is laminated on the ion sensitive insulating film.

(Supplementary Note 11)

The TFT ion sensor as depicted in any one of Supplementary Notes 1 to 9, wherein an enzyme which changes hydrogen ion concentration in the vicinity of the ion sensitive insulating film by reacting with a substrate is solidified on the ion sensitive insulating film.

(Supplementary Note 12)

The TFT ion sensor as depicted in any one of Supplementary Notes 1 to 9, wherein protein, sugar, DNA, or RNA which exhibits sensitivity for a specific bio-substance and generates a potential change by a mutual action with the bio-substance is disposed on the ion sensitive insulating film.

(Supplementary Note 13)

The TFT ion sensor as depicted in any one of Supplementary Notes 1 to 12, wherein:

the gate insulating film and the ion sensitive insulating film are formed with substantially a same material; and film thickness of the gate insulating film is greater than film thickness of the ion sensitive insulating film.

(Supplementary Note 14)

The TFT ion sensor as depicted in any one of Supplementary Notes 1 to 12, wherein a relative dielectric constant of an substantial structural material of the ion sensitive insulating film is larger than a relative dielectric constant of an substantial structural material of the gate insulating film.

(Supplementary Note 15)
The TFT ion sensor as depicted in any one of Supplementary Notes 1 to 14, wherein
hole accumulation does not occur in the semiconductor active layer.

(Supplementary Note 16)
The TFT ion sensor as depicted in any one of Supplementary Notes 1 to 15, wherein
the semiconductor active layer is formed with an oxide semiconductor.

(Supplementary Note 17)
The TFT ion sensor as depicted in any one of Supplementary Notes 1 to 16, wherein
the actual structural material of the gate insulating film is a monolayer film formed with one selected from silicon oxide, silicon nitride, and aluminum oxide or a laminated film formed of two or more of those.

(Supplementary Note 18)
The TFT ion sensor as depicted in any one of Supplementary Notes 1 to 17, wherein
a defect density in an interface between the semiconductor active layer and the ion sensitive insulating film is suppressed to $1 \times 10^{21}$ cm$^{-3}$ or less.

(Supplementary Note 19)
A TFT ion sensor apparatus which includes:
a TFT ion sensor which includes a semiconductor active layer to which a source electrode and a drain electrode are connected; a gate insulating film and a gate electrode provided on one of surfaces of the semiconductor active layer; an ion sensitive insulating film provided on the other surface of the semiconductor active layer; and a reference electrode provided at a position spatially isolated from the ion sensitive insulating film, wherein an electrostatic capacitance per unit area of the ion sensitive insulating film is larger than an electrostatic capacitance per unit area of the gate insulating film; and
a detection circuit which: supplies a constant potential to the reference electrode by having a potential of the source electrode as a reference; supplies a constant potential difference between the source electrode and the drain electrode; controls the potential difference between the gate electrode and the source electrode so that a constant current flows between the source electrode and the drain electrode; and outputs the potential difference between the gate electrode and the source electrode or a voltage corresponding to the potential difference.

(Supplementary Note 20)
The TFT ion sensor apparatus as depicted in Supplementary Note 19, wherein:
the detection circuit includes a constant voltage circuit which fixes the potential difference between the source electrode and the drain electrode, and a constant current circuit connected to the source electrode;
the constant voltage circuit includes a voltage follower circuit whose input node is connected to the source electrode, and a constant voltage source whose one end is connected to an output node of the voltage follower circuit and whose other end is connected to the drain electrode; and
an output voltage of the voltage follower circuit is outputted as a voltage corresponding to the potential difference between the gate electrode and the source electrode.

(Supplementary Note 21)
A measuring method using a TFT ion sensor which includes a semiconductor active layer to which a source electrode and a drain electrode are connected; a gate insulating film and a gate electrode provided on one of surfaces of the semiconductor active layer; an ion sensitive insulating film provided on the other surface of the semiconductor active layer; and a reference electrode provided at a position spatially isolated from the ion sensitive insulating film, wherein an electrostatic capacitance per unit area of the ion sensitive insulating film is larger than an electrostatic capacitance per unit area of the gate insulating film, and the method includes:
filling a space between the ion sensitive insulating film and the reference electrode with a sensing-target substance;
controlling a potential difference between the source electrode and the gate electrode so that a constant current flows between the source electrode and the drain electrode; and
reading out the potential difference between the source electrode and the gate electrode.

(Supplementary Note 22)
A measuring method using a TFT ion sensor which includes a semiconductor active layer to which a source electrode and a drain electrode are connected; a gate insulating film and a gate electrode provided on one of surfaces of the semiconductor active layer; an ion sensitive insulating film provided on the other surface of the semiconductor active layer; and a reference electrode provided at a position spatially isolated from the ion sensitive insulating film, wherein an electrostatic capacitance per unit area of the ion sensitive insulating film is larger than an electrostatic capacitance per unit area of the gate insulating film, and the method includes:
filling a space between the ion sensitive insulating film and the reference electrode with a sensing-target substance;
controlling a current flown between the source electrode and the drain electrode so that a potential difference between the gate electrode and the source electrode becomes constant; and
reading out the current flown in the source electrode or the drain electrode.

INDUSTRIAL APPLICABILITY

As the possible industrial applicability of the present invention, there is considered a highly sensitive ion sensor element associated with biological, medical, and environmental fields. Especially, the use of the oxide semiconductor TFT with which hole accumulation does not occur and a perfect depletion type property tends to generate makes it possible to acquire the highly sensitive sensing property that is implemented by the present invention. Further, the oxide semiconductor is transparent for visible light, so that the property of the oxide semiconductor TFT in a visible light irradiated state exhibits no difference in the property under a dark state. This is greatly different from a silicon-type TFT with which the electric property varies for a visible light irradiated state and a dark state. By the use of such characteristic of the oxide semiconductor, the present invention can be utilized for the ion sensor that is capable of performing highly sensitive sensing both in the dark state and the visible light irradiated state.

What is claimed is:
1. A thin film transistor (TFT) ion sensor, comprising:
a semiconductor active layer to which a source electrode and a drain electrode are connected;
a gate insulating film and a gate electrode provided on one of surfaces of the semiconductor active layer;
an ion sensitive insulating film provided on the other surface of the semiconductor active layer, an electrostatic capacitance per unit area of the ion sensitive insulating film being n-times (n>1) greater than an electrostatic capacitance per unit area of the gate insulating film;

a reference electrode provided at a position spatially isolated from the ion sensitive insulating film; and a voltage detection unit configured to read out a potential difference between the source electrode and the gate electrode that is n-times greater than a potential difference between the source electrode and the gate electrode when the electrostatic capacitance per unit area of the ion sensitive insulating film is equivalent to the electrostatic capacitance per unit area of the gate insulating film.

2. The TFT ion sensor as claimed in claim 1, wherein the potential difference between the source electrode and the gate electrode is a potential difference acquired by multiplying a value of a ratio that is acquired by dividing the electrostatic capacitance per unit area of the ion sensitive insulating film by the electrostatic capacitance per unit area of the gate insulating film to a potential difference generated between the ion sensitive insulating film and a sensing-target substance that is disposed on the ion sensitive insulating film.

3. The TFT ion sensor as claimed in claim 1, further comprising:

a voltage control unit which controls the potential difference between the source electrode and the gate electrode so that a constant current flows between the source electrode and the drain electrode.

4. The TFT ion sensor as claimed in claim 1, wherein the gate electrode, the gate insulating film, the semiconductor active layer, the source electrode as well as the drain electrode, and the ion sensitive insulating film are provided in this order on a substrate.

5. The TFT ion sensor as claimed in claim 1, wherein:

a thermal oxide film, the source electrode, the drain electrode, the semiconductor active layer, the gate insulating film, and the gate electrode are provided in this order on a silicon substrate; and an opening part is provided in the silicon substrate so that the thermal oxide film located under the semiconductor active layer is exposed.

6. The TFT ion sensor as claimed in claim 1, wherein:

the semiconductor active layer, the source electrode, the drain electrode, the gate insulating film, and the gate electrode are provided in this order on an insulating substrate; and a recessed part is provided on the insulating substrate on an opposite side from the semiconductor active layer so that a thin part of the insulating substrate is exposed.

7. The TFT ion sensor as claimed in claim 1, wherein the ion sensitive insulating film is a monolayer film formed with one selected from tantalum oxide, hafnium oxide, aluminum oxide, barium titanate, strontium titanate, and a silicon nitride, or a laminated film formed with two or more of tantalum oxide, hafnium oxide, aluminum oxide, barium titanate, strontium titanate, and a silicon nitride.

8. The TFT ion sensor as claimed in claim 1, wherein an ion selective sensitive film exhibiting sensitivity for a specific ion is laminated on the ion sensitive insulating film.

9. The TFT ion sensor as claimed in claim 1, wherein an enzyme which changes hydrogen ion concentration in vicinity of the ion sensitive insulating film by reacting with a substrate is solidified on the ion sensitive insulating film.

10. The TFT ion sensor as claimed in claim 1, wherein protein, sugar, DNA, or RNA which exhibits sensitivity for a specific bio-substance and generates a potential change by a mutual action with the bio-substance is disposed on the ion sensitive insulating film.

11. The TFT ion sensor as claimed in claim 1, wherein:

the gate insulating film and the ion sensitive insulating film are formed with substantially a same material, and a film thickness of the gate insulating film is thicker than a film thickness of the ion sensitive insulating film.

12. The TFT ion sensor as claimed in claim 1, wherein a relative dielectric constant of a substantial structural material of the ion sensitive insulating film is larger than a relative dielectric constant of a substantial structural material of the gate insulating film.

13. The TFT ion sensor as claimed in claim 1, wherein hole accumulation does not occur in the semiconductor active layer.

14. The TFT ion sensor as claimed in claim 1, wherein the semiconductor active layer is formed with an oxide semiconductor.

15. The TFT ion sensor as claimed in claim 1, wherein a substantial structural material of the gate insulating film is a monolayer film formed with one selected from silicon oxide, silicon nitride, and aluminum oxide or a laminated film formed of two or more of silicon oxide, silicon nitride, and aluminum oxide.

16. The TFT ion sensor as claimed in claim 1, wherein a defect density in an interface between the semiconductor active layer and the ion sensitive insulating film is suppressed to $1\times10^{21}$ cm$^{-3}$ or less.

17. A thin film transistor (TFT) ion sensor comprising:

a semiconductor active layer to which a source electrode and a drain electrode are connected;

a gate insulating film and a gate electrode provided on one of surfaces of the semiconductor active layer;

an ion sensitive insulating film provided on the other surface of the semiconductor active layer, an electrostatic capacitance per unit area of the ion sensitive insulating film being n-times (n>1) greater than an electrostatic capacitance per unit area of the gate insulating film;

a reference electrode provided at a position spatially isolated from the ion sensitive insulating film; and a current detection unit configured to read out a current flow in the source electrode or the drain electrode that is n-times greater than a current flow in the source electrode or the drain electrode when the electrostatic capacitance per unit area of the ion sensitive insulating film is equivalent to the electrostatic capacitance per unit area of the gate insulating film.

18. The TFT ion sensor as claimed in claim 17, further comprising a current control unit which controls the current flown between the source electrode and the drain electrode so that the potential difference between the gate electrode and the source electrode becomes constant.

19. A thin film transistor (TFT) ion sensor apparatus, comprising:

a TFT ion sensor which comprises a semiconductor active layer to which a source electrode and a drain electrode are connected;

a gate insulating film and a gate electrode provided on one of surfaces of the semiconductor active layer;

an ion sensitive insulating film provided on the other surface of the semiconductor active layer, an electrostatic capacitance per unit area of the ion sensitive insulating film being n-times (n>1) greater than an electrostatic capacitance per unit area of the gate insulating film;

a reference electrode provided at a position spatially isolated from the ion sensitive insulating film; and
a detection circuit which
supplies a constant potential to the reference electrode by having a potential of the source electrode as a reference,
supplies a constant potential difference between the source electrode and the drain electrode,
controls the potential difference between the gate electrode and the source electrode so that a constant current flows between the source electrode and the drain electrode, and
outputs the potential difference between the gate electrode and the source electrode or a voltage corresponding to the potential difference that is n-times greater than a potential difference between the gate electrode and the source electrode when the electrostatic capacitance per unit area of the ion sensitive insulating film is equivalent to the electrostatic capacitance per unit area of the gate insulating film.

20. The TFT ion sensor apparatus as claimed in claim 19, wherein:
the detection circuit comprises
a constant voltage circuit which fixes the potential difference between the source electrode and the drain electrode, the constant voltage circuit comprising
a voltage follower circuit having an input node connected to the source electrode, an output voltage of the voltage follower circuit being output as a voltage corresponding to the potential difference between the gate electrode and the source electrode, and
a constant voltage source having one end connected to an output node of the voltage follower circuit and having another end connected to the drain electrode; and
a constant current circuit connected to the source electrode.

* * * * *